United States Patent
Ogawa

(10) Patent No.: US 10,522,145 B2
(45) Date of Patent: Dec. 31, 2019

(54) INFORMATION PROCESSING APPARATUS AND INFORMATION PROCESSING METHOD

(71) Applicant: SONY CORPORATION, Tokyo (JP)

(72) Inventor: Hiroaki Ogawa, Chiba (JP)

(73) Assignee: SONY CORPORATION, Tokyo (JP)

( * ) Notice: Subject to any disclaimer, the term of this patent is extended or adjusted under 35 U.S.C. 154(b) by 0 days.

(21) Appl. No.: 16/077,336

(22) PCT Filed: Nov. 25, 2016

(86) PCT No.: PCT/JP2016/085030
§ 371 (c)(1),
(2) Date: Aug. 10, 2018

(87) PCT Pub. No.: WO2017/149868
PCT Pub. Date: Sep. 8, 2017

(65) Prior Publication Data
US 2019/0057696 A1    Feb. 21, 2019

(30) Foreign Application Priority Data

Mar. 1, 2016   (JP) .................... 2016-039176

(51) Int. Cl.
*G10L 21/00* (2013.01)
*G10L 15/22* (2006.01)
(Continued)

(52) U.S. Cl.
CPC .......... *G10L 15/22* (2013.01); *A61B 1/00039* (2013.01); *A61B 1/00183* (2013.01);
(Continued)

(58) Field of Classification Search
None
See application file for complete search history.

(56) References Cited

U.S. PATENT DOCUMENTS 6,463,361 B1   10/2002   Wang et al.
7,409,344 B2 *  8/2008   Gurram .................. G06F 3/167
                                                              379/88.01
(Continued)

FOREIGN PATENT DOCUMENTS

AU    3721195 A      4/1996
CA    2200716 A1     3/1996
(Continued)

OTHER PUBLICATIONS

Extended European Search Report of EP Patent Application No. 16892703.6, dated Dec. 11, 2018, 12 pages.
(Continued)

*Primary Examiner* — Satwant K Singh
(74) *Attorney, Agent, or Firm* — Chip Law Group

(57) ABSTRACT

An information processing apparatus and information processing method are provided to interpret the meaning of a result of voice recognition adaptively to the situation in collecting voice. The information processing apparatus includes a semantic interpretation unit that interprets a meaning of a recognition result of a collected voice of a user on a basis of the recognition result and context information in collecting the voice.

20 Claims, 16 Drawing Sheets

(51) Int. Cl.
  *G10L 25/51* (2013.01)
  *G06F 3/01* (2006.01)
  *G10L 15/24* (2013.01)
  *G06F 3/16* (2006.01)
  *A61B 1/00* (2006.01)
  *G10L 15/18* (2013.01)
  *B25J 13/00* (2006.01)
  *G05D 1/00* (2006.01)

(52) U.S. Cl.
  CPC ......... *A61B 1/00188* (2013.01); *B25J 13/003* (2013.01); *G06F 3/01* (2013.01); *G06F 3/167* (2013.01); *G10L 15/1815* (2013.01); *G10L 15/24* (2013.01); *G10L 25/51* (2013.01); *G05D 1/00* (2013.01); *G10L 2015/223* (2013.01)

(56) References Cited

U.S. PATENT DOCUMENTS

| | | | | |
|---|---|---|---|---|
| 7,672,851 | B2* | 3/2010 | Gurram | G06F 3/167 704/270 |
| 8,140,335 | B2* | 3/2012 | Kennewick | G06Q 30/0261 704/257 |
| 8,326,627 | B2* | 12/2012 | Kennewick | G06Q 30/0261 704/257 |
| 8,370,147 | B2* | 2/2013 | Kennewick | G06Q 30/0261 704/257 |
| 8,452,598 | B2* | 5/2013 | Kennewick | G06Q 30/0261 704/257 |
| 8,571,851 | B1* | 10/2013 | Tickner | G06F 17/2785 704/1 |
| 8,719,026 | B2* | 5/2014 | Kennewick | G06Q 30/0261 704/257 |
| 8,788,271 | B2* | 7/2014 | James | G10L 15/265 704/275 |
| 8,983,839 | B2* | 3/2015 | Kennewick | G06Q 30/0261 704/254 |
| 9,620,113 | B2* | 4/2017 | Kennewick | G06Q 30/0261 |
| 10,347,248 | B2* | 7/2019 | Kennewick | G06Q 30/0261 |
| 2002/0183894 | A1 | 12/2002 | Wang et al. | |
| 2005/0033580 | A1 | 2/2005 | Wang et al. | |
| 2010/0241431 | A1 | 9/2010 | Weng et al. | |
| 2011/0125487 | A1 | 5/2011 | Ylonen | |
| 2012/0287284 | A1 | 11/2012 | Jacobsen et al. | |
| 2013/0300649 | A1 | 11/2013 | Parkinson et al. | |
| 2014/0222252 | A1 | 8/2014 | Matters et al. | |
| 2015/0120089 | A1* | 4/2015 | Peel | B60T 7/16 701/2 |
| 2016/0232890 | A1* | 8/2016 | Pfalzgraf | G10L 15/22 |

FOREIGN PATENT DOCUMENTS

| | | |
|---|---|---|
| CN | 102428440 A | 4/2012 |
| CN | 103620527 A | 3/2014 |
| CN | 103857583 A | 6/2014 |
| CN | 107253493 A | 10/2017 |
| DE | 102011084366 A1 | 4/2013 |
| DE | 112012004263 A5 | 7/2014 |
| DE | 112012007286 A5 | 4/2016 |
| EP | 2409218 A1 | 1/2012 |
| JP | 64-035893 A | 2/1989 |
| JP | 2001-133283 A | 5/2001 |
| JP | 2001-188551 A | 7/2001 |
| JP | 2002-094980 A | 3/2002 |
| JP | 2007-122580 A | 5/2007 |
| JP | 2011-198304 A | 10/2011 |
| JP | 2015-047309 A | 3/2015 |
| JP | 2016-502355 A | 1/2016 |
| WO | 96/09587 A1 | 3/1996 |
| WO | 2010/107526 A1 | 9/2010 |
| WO | 2012/154938 A1 | 11/2012 |
| WO | 2013/053776 A2 | 4/2013 |
| WO | 2014/088845 A1 | 6/2014 |
| WO | 2014/107219 A1 | 7/2014 |

OTHER PUBLICATIONS

International Search Report and Written Opinion of PCT Application No. PCT/JP2016/085030, dated Feb. 14, 2017, 11 pages of ISRWO.

* cited by examiner

| SEMANTIC REPRESENTATION | INTERNAL SOUND COLLECTOR | EXTERNAL SOUND COLLECTOR | FIRST REMOTE SOUND COLLECTOR | SECOND REMOTE SOUND COLLECTOR |
|---|---|---|---|---|
| 1260 | 1262 | 1264 | 1266 | 1268 |
| GO_RIGHT_SUBJECTIVE | GO_RIGHT | if FRONT_VOICE<br>GO_LEFT<br>else if RIGHT_VOICE<br>GO_FRONT<br>else if LEFT_VOICE<br>BACK_FORWARD<br>else<br>BACK_RIGHT | if FRONTVIEW<br>GO_RIGHT<br>else<br>BACK_LEFT | GO_DIR(MAP_RIGHT) |
| ... | ... | ... | ... | ... |

INFORMATION PROCESSING APPARATUS AND INFORMATION PROCESSING METHOD

CROSS REFERENCE TO RELATED APPLICATIONS

This application is a U.S. National Phase of International Patent Application No. PCT/JP2016/085030 filed on Nov. 25, 2016, which claims priority benefit of Japanese Patent Application No. JP 2016-039176 filed in the Japan Patent Office on Mar. 1, 2016. Each of the above-referenced applications is hereby incorporated herein by reference in its entirety.

TECHNICAL FIELD

The present disclosure relates to an information processing apparatus, an information processing method, and a program.

BACKGROUND ART

Various techniques for controlling a device capable of autonomous movement, such as cars, robots, and drones, have been recently developed.

In one example, Patent Literature 1 below discloses a technique for controlling the actuation of a robot on the basis of a user operation on a webpad. In addition, Patent Literature 2 below discloses a technique for controlling the actuation of a robot in response to a touch operation on a CG image displayed on a touch screen.

CITATION LIST

Patent Literature

Patent Literature 1: JP 2014-505934T
Patent Literature 2: JP 2012-171024A

DISCLOSURE OF INVENTION

Technical Problem

Meanwhile, it is also desirable to give a command to a device capable of autonomous movement by means of a voice. In one example, the doctor's hands are full in performing surgery, so there is a great demand for giving a command to a relevant device by voice.

However, assuming that the technique disclosed in Patent Literatures 1 or 2 is applied to a case where a voice command is given to a device, the techniques disclosed in Patent Literatures 1 and 2 interpret the meaning of a recognition result of the voice without considering the situation in collecting voice. Thus, in the techniques disclosed above, in one example, the recognition result will be more likely to be interpreted as a meaning different from that intended by the user disadvantageously.

Thus, the present disclosure provides a novel and improved information processing apparatus, information processing method, and program, capable of interpreting the meaning of a result of voice recognition adaptively to the situation in collecting voice.

Solution to Problem

According to the present disclosure, there is provided an information processing apparatus including: a semantic interpretation unit configured to interpret a meaning of a recognition result of a collected voice of a user on a basis of the recognition result and context information in collecting the voice.

In addition, according to the present disclosure, there is provided an information processing method including: interpreting, by a processor, a meaning of a recognition result of a collected voice of a user on a basis of the recognition result and context information in collecting the voice.

In addition, according to the present disclosure, there is provided a program causing a computer to function as: a semantic interpretation unit configured to interpret a meaning of a recognition result of a collected voice of a user on a basis of the recognition result and context information in collecting the voice.

Advantageous Effects of Invention

According to the present disclosure as described above, it is possible to interpret the meaning of a voice recognition result adaptively to the situation in collecting voice. Note that the effects described herein are not necessarily limited, and any of the effects described in this disclosure may be applied.

BRIEF DESCRIPTION OF DRAWINGS

FIG. 6 is a diagram illustrated to describe an exemplary configuration of a disambiguation knowledge DB 126 according to the first embodiment.

MODE(S) FOR CARRYING OUT THE INVENTION

Figure 1:
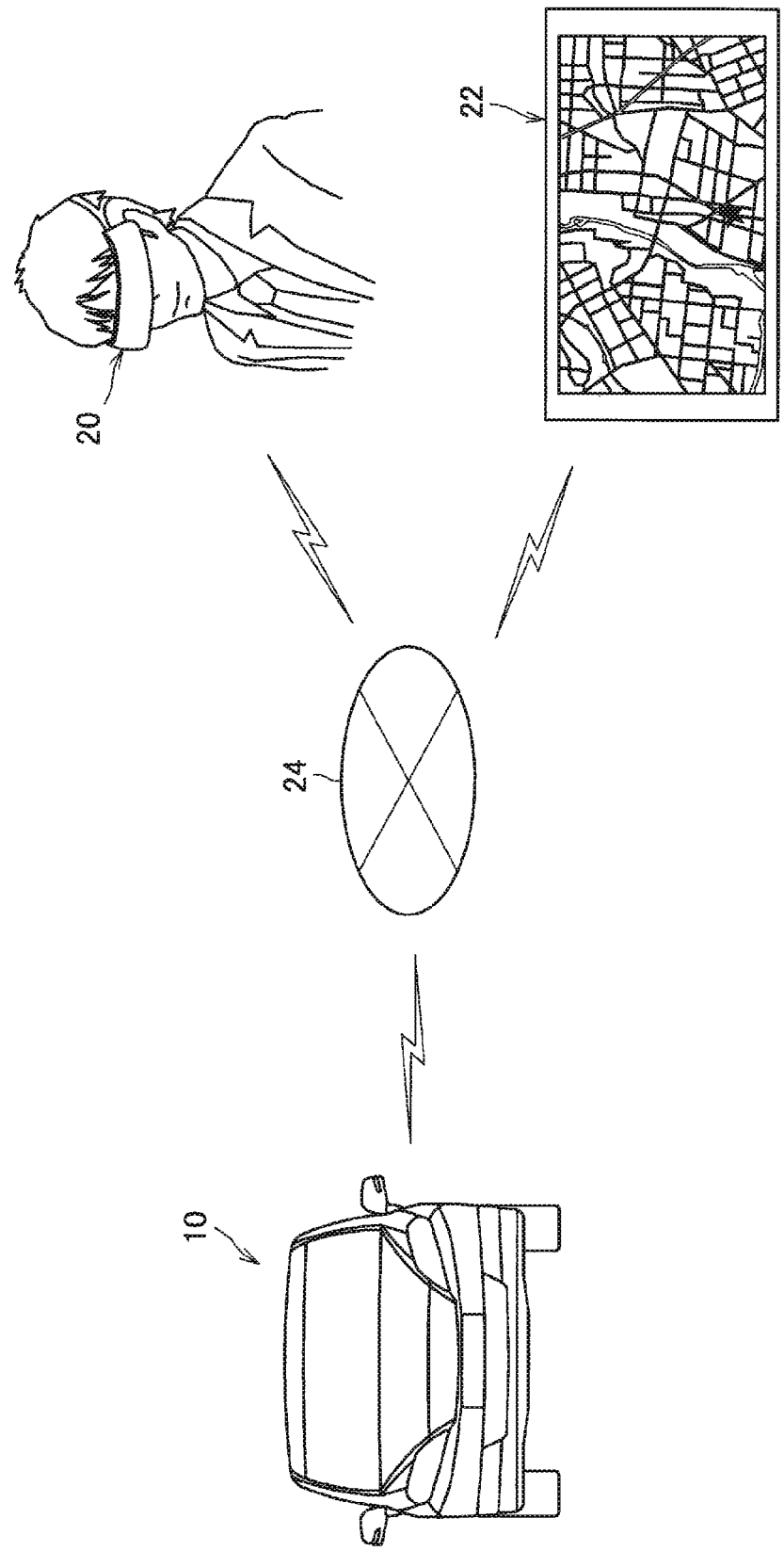
FIG. 1 is a diagram illustrated to describe an exemplary configuration of an information processing system according to a first embodiment.

Hereinafter, (a) preferred embodiment(s) of the present disclosure will be described in detail with reference to the appended drawings. Note that, in this specification and the appended drawings, structural elements that have substantially the same function and structure are denoted with the same reference numerals, and repeated explanation of these structural elements is omitted.

Further, in the present specification and drawings, in some cases, a plurality of components having substantially the same functional configuration are distinguished by addition of an alphabetic suffix. In one example, the plurality of components having substantially the same functional configuration are distinguished, like a car 10*a* and a car 10*b*, as necessary. However, unless it is necessary to distinguish particularly a plurality of components having substantially the same functional configuration from each other, only the same reference numeral is attached. In one example, unless it is necessary to distinguish particularly the car 10*a* and the car 10*b* from each other, they simply referred to as car 10.

Further, the "modes for carrying out the invention" will be described according to the order of listing shown below.
1. Background
2. First embodiment
3. Second embodiment
4. Third embodiment
5. Fourth embodiment
6. Modification «1. Background»

The background leading to the technical matters stated in the present disclosure is first described to clarify the features of the present disclosure. In related art, in one example, various devices capable of autonomous movement such as cars, robots, and drones having an automatic driving function have been developed. Then, such device can be equipped with a voice recognition function. In one example, in a case where the user utters a command "Raise the hand" to a robot, it is possible to perform control in such a way that the robot lifts the arm upward by recognizing the voice by the robot.

Further, it is also possible to operate the robot by remote control from the outside. In one example, in a case where the user located away from the robot utters a command to the robot through a terminal such as a smartphone, the terminal first transmits the collected voice to the robot. Then, the robot is capable of executing the control based on the recognition result of the voice by recognizing the received voice.

Further, it is also possible for the user to give a command to a robot by voice while viewing an image captured by a camera mounted on the robot through a display device such as a wearable device.

Moreover, in the case where the user gives a command to the robot by voice, the input voice signal of the user is converted into text by voice recognition, and the converted text is subjected to semantic interpretation, so the robot interprets the meaning of the command.

<1-1. Summary of Problems>

In the known technique, however, the robot is incapable of properly interpreting the meaning of the voice of the command given by the user in some cases. In one example, there is a case of a command including a relative word expression, such as "right" or "left", for example, a voice "Go right!" In this case, if the robot performs interpretation only on the basis of a result of voice recognition, the robot is more likely to disadvantageously interpret the recognition result as a meaning different from the user's intention. More specifically, the robot is incapable of specifying whether a reference direction is the right relative to the user's orientation or relative to the robot's orientation only on the basis of the voice recognition result.

Further, the same voice (e.g., "Go right!") may have meanings changed by the user's intention depending on the situation in which the voice is uttered. In one example, in a case where the user utters a command while viewing an image captured by a camera mounted on the robot, the user often wants the robot to move in the right direction on the image. In addition, in one example, in a case where the user gives a command while viewing a screen bird's-eye view of the current position of the robot, such as a map screen, the user often wants the robot to move in the right direction on the screen.

Thus, the present disclosure is made with considering the above-mentioned circumstances as one point of view. According to the present disclosure, in a case where a command is uttered to a device, it is possible to interpret the meaning of the command on the basis of the voice recognition result and context information in collecting voice. This makes it possible to specify the meaning of the command so that it conforms to the user's intuition depending on the situation in which the command is uttered. The embodiments of such present disclosure will be described sequentially below.

«2. First Embodiment»

<2-1. Configuration of Information Processing System>

A first embodiment is first described. In the first embodiment, a case where the user moves a car 10 by giving a command by voice to the car 10 having the automatic driving function is assumed. FIG. 1 is a diagram illustrated to describe a configuration of an information processing system according to the first embodiment. As illustrated in FIG. 1, the information processing system according to the first embodiment includes the car 10, an HMD 20, a tablet terminal 22, and a communication network 24.

{2-1-1. Car 10}

The car 10 is an example of an information processing apparatus and a device according to the present disclosure. The car 10 has a voice recognition function, and so it is possible to control the movement of the car 10 on the basis of a recognition result of the voice.

Figure 2A:
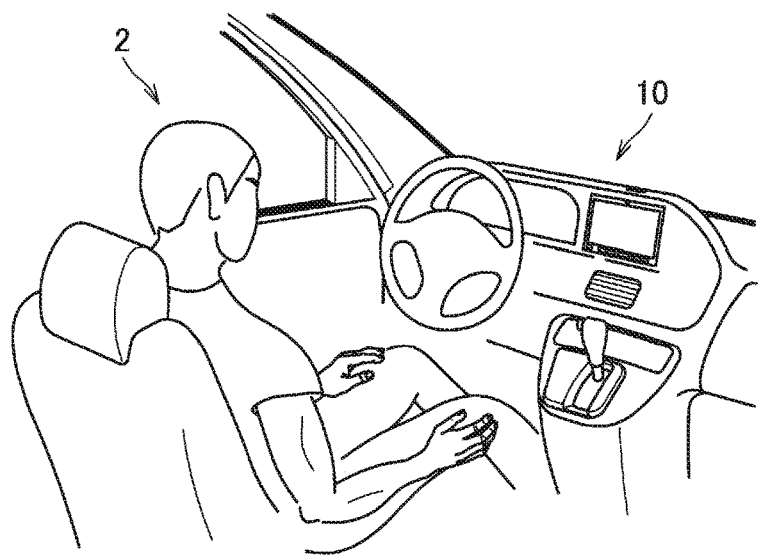
FIGS. 2A and 2B are diagrams illustrated to describe how a user gives a command by voice inside or outside a car 10.
Figure 2B:
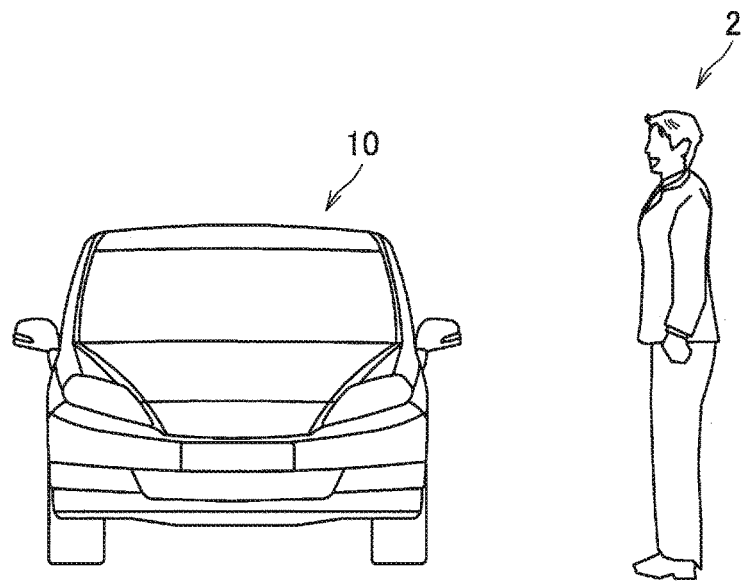

In one example, as illustrated in FIG. 2A, the car 10 is capable of collecting the voice of a user 2 who is riding in it through an internal sound collector 100 installed inside the car 10, thereby recognizing the collected voice. In addition, as illustrated in FIG. 2B, the car 10 is capable of collecting the voice of the user 2 located outside the car 10 through an external sound collector 102 installed outside the car 10, thereby recognizing the collected voice.

Further, the car 10 may have an imaging unit (not shown) for capturing an image in the front direction of the car 10 and an imaging unit (not shown) for capturing an image in the rear direction thereof. Moreover, the imaging unit may be installed outside the car 10, may be installed inside the car 10, or may be installed both outside and inside the car 10.

Further, as illustrated in FIG. 1, the car 10 is capable of transmitting and receiving information to and from the HMD 20 and the tablet terminal 22 via the communication network 24. In this regard, the HMD 20 and the tablet terminal 22 are typically used by a user located remotely of the car 10. However, it is not limited to this example, specifically the HMD 20 and the tablet terminal 22 can be used by a user who is riding in the car 10.

In one example, the car 10 is capable of transmitting an image or the like captured by an imaging unit to the HMD 20 or the tablet terminal 22. In addition, the car 10 is capable of receiving the user's voice, which is collected by the HMD 20 or the tablet terminal 22, from each of the HMD 20 and the tablet terminal 22. Then, the car 10 is capable of recognizing the voice of the command received from the HMD 20 or the tablet terminal 22 and performing control on the basis of the recognition result.

{2-1-2. HMD 20}

The HMD 20 is a wearable device. The HMD 20 includes a display unit for displaying a display screen and a first remote sound collector 200 for collecting the user's voice. In addition, the HMD 20 is capable of transmitting and receiving information to and from the car 10 via the communication network 24. In one example, the HMD 20 receives an image, which is captured by the imaging unit installed in the car 10, from the car 10. Then, it is possible to display the received image on the display unit.

Further, the first remote sound collector 200 collects the voice of a user's command given to the car 10 in displaying the image received from the car 10 or the like. Then, the HMD 20 is capable of transmitting, to the car 10, the voice collected by the first remote sound collector 200 and the context information in collecting voice (e.g., information indicating which direction the image of the car 10 is displayed on the display unit in collecting voice).

{2-1-3. Tablet Terminal 22}

The tablet terminal 22 includes a display unit for displaying a display screen and a second remote sound collector 220 for collecting the user's voice. In one example, the display unit displays various display screens such as a map screen. In addition, the second remote sound collector 220 collects the voice of the user's command given to the car 10 in displaying the map screen. Then, the tablet terminal 22 transmits the collected voice and the context information in collecting voice (e.g., information indicating the relationship between display direction and cardinal point of the map screen displayed on the display unit) to the car 10 via the communication network 24.

{2-1-4. Communication Network 24}

The communication network 24 is a wired or wireless transmission channel of information transmitted from a device connected to the communication network 24. The communication network 24 may include a public line network such as telephone networks, the Internet, and satellite communication networks, and various local area networks (LANs) and wide area networks (WANs) including Ethernet (registered trademark). In addition, the communication network 24 may include a leased line network such as Internet protocol-virtual private network (IP-VPN).

<2-2. Configuration>

Figure 3:
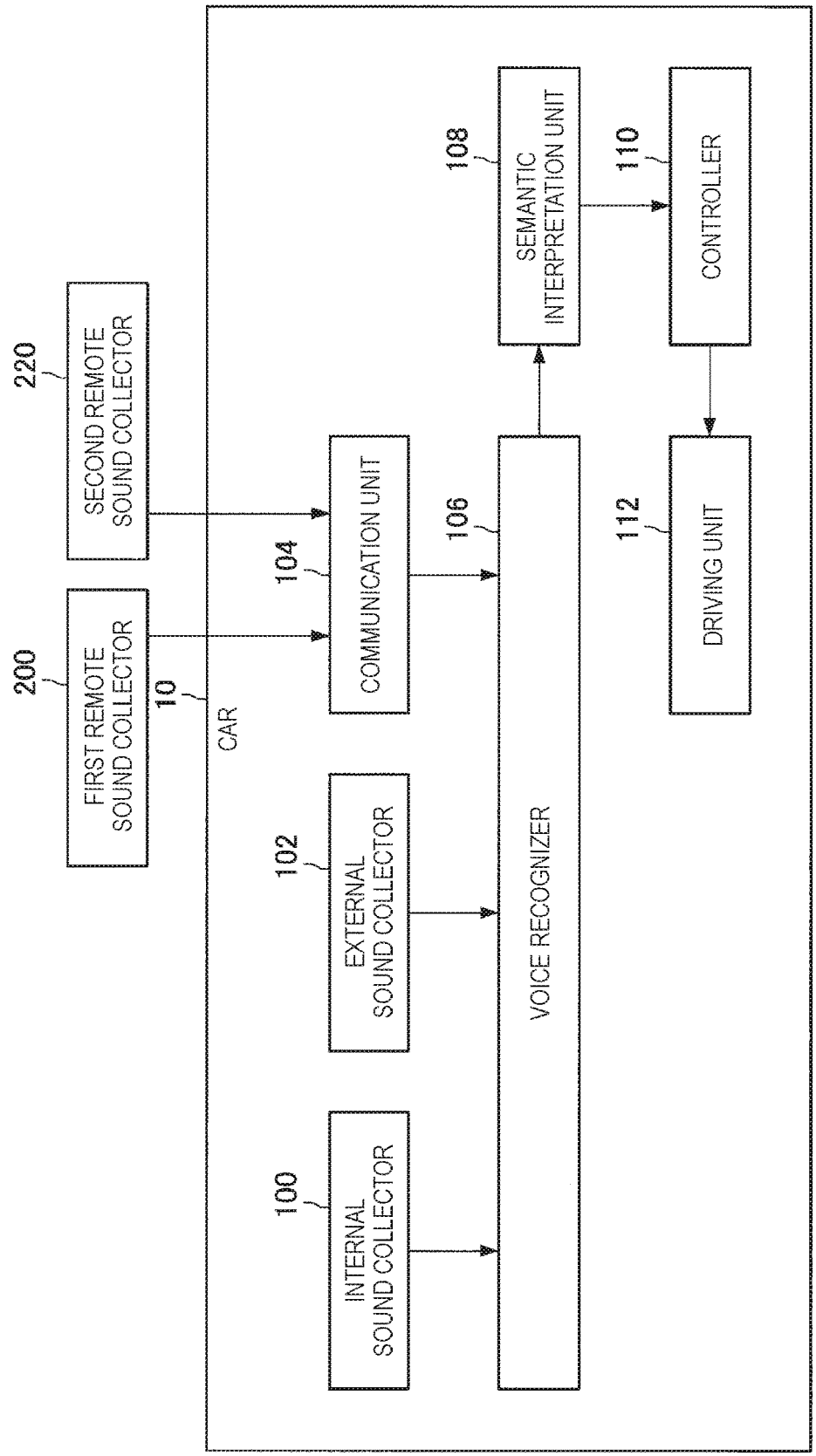
FIG. 3 is a functional block diagram illustrating an exemplary configuration of the car 10 according to the first embodiment.

The configuration of the information processing system according to the first embodiment is described above. The configuration of the car 10 according to the first embodiment is now described in detail. FIG. 3 is a functional block diagram illustrating an exemplary configuration of the car 10 according to the first embodiment. As illustrated in FIG. 3, the car 10 includes an internal sound collector 100, an external sound collector 102, a communication unit 104, a voice recognizer 106, a semantic interpretation unit 108, a controller 110, and a driving unit 112.

{2-2-1. Internal Sound Collector 100}

The internal sound collector 100 is a sound collector installed inside the car. In one example, the internal sound collector 100 detects the sound (aerial vibration) inside the car and converts it into an electrical signal. In addition, the internal sound collector 100 transfers the collected voice and the context information in collecting voice (e.g., information indicating that the voice is collected by the internal sound collector 100, etc.) to the voice recognizer 106.

{2-2-2. External Sound Collector 102}

The external sound collector 102 is a sound collector installed outside the car 10. In one example, the external sound collector 102 detects sound outside the car 10 and converts it into an electrical signal. In addition, the external sound collector 102 transfers the collected voice and the context information in collecting voice (e.g., the arrival direction or arrival time of the voice, etc.) to the voice recognizer 106.

{2-2-3. Communication Unit 104}

The communication unit 104 transmits and receives information to and from other devices, in one example, via the communication network 24. In one example, the communication unit 104 receives the collected voice and the context information in collecting voice from the HMD 20 or the tablet terminal 22.

Further, the communication unit 104 transfers the received voice and the context information to the voice recognizer 106.

{2-2-4. Voice Recognizer 106}

The voice recognizer 106 recognizes the voice transferred from the internal sound collector 100, the external sound collector 102, or the communication unit 104, and converts it into a character string. In addition, the voice recognizer 106 transfers a voice recognition result and the received context information to the semantic interpretation unit 108.

{2-2-5. Semantic Interpretation Unit 108}

Figure 4:
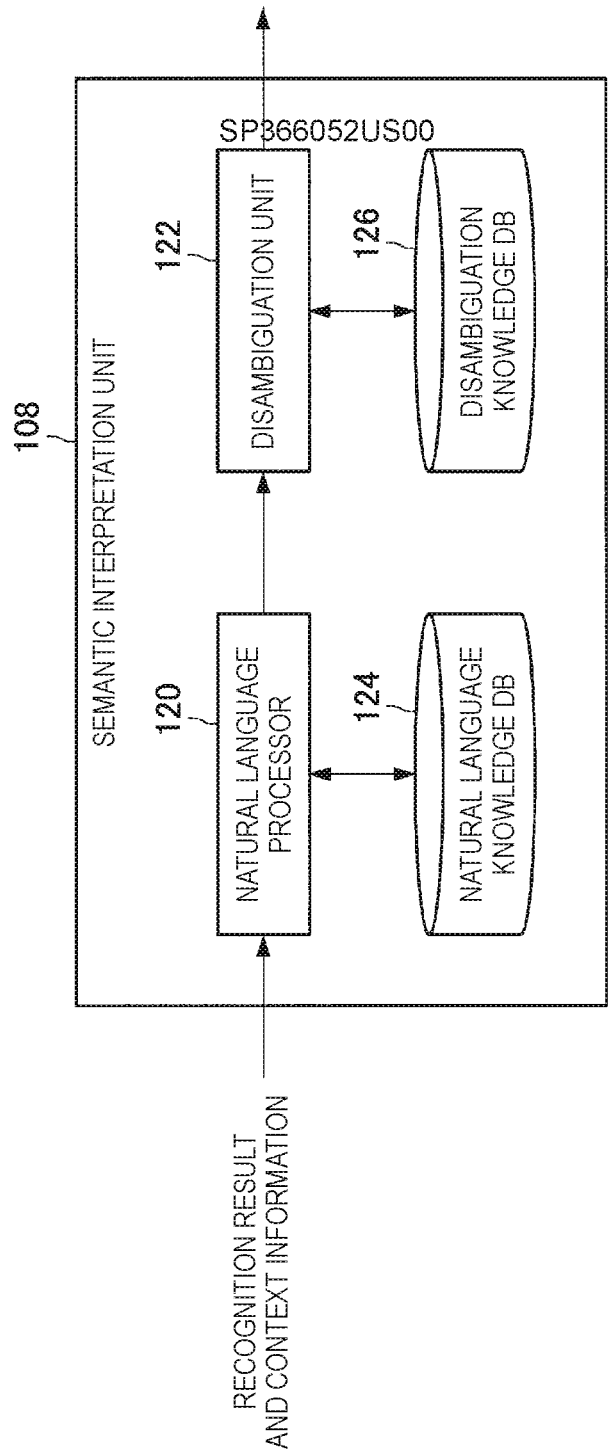
FIG. 4 is a functional block diagram illustrating an exemplary configuration of a semantic interpretation unit 108 according to the first embodiment.

The semantic interpretation unit 108 interprets a meaning of the recognition result obtained by the voice recognizer 106 on the basis of the recognition result and the context information in collecting voice. FIG. 4 is a functional block diagram illustrating a detailed exemplary configuration of the semantic interpretation unit 108. As illustrated in FIG. 4, the semantic interpretation unit 108 includes a natural language processor 120 and a disambiguation unit 122.

{2-2-6. Natural Language Processor 120}

The natural language processor 120 converts the recognition result obtained by the voice recognizer 106 into a semantic representation. In one example, the natural language processor 120 refers to a natural language knowledge DB 124 on the basis of the recognition result to convert the recognition result into the semantic representation.

Figure 5:
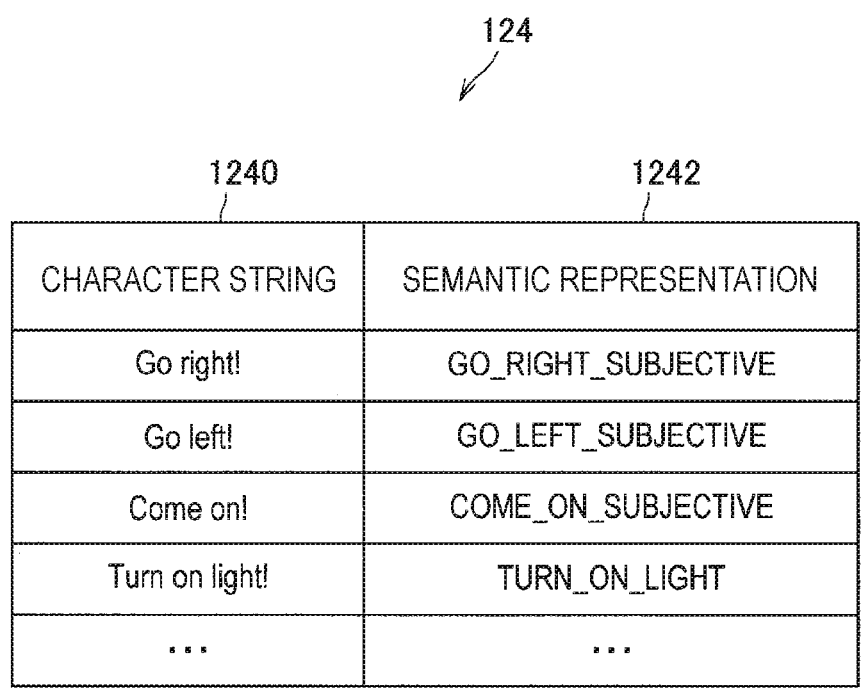
FIG. 5 is a diagram illustrated to describe an exemplary configuration of a natural language knowledge DB 124 according to the first embodiment.

Here, the natural language knowledge DB 124 is a database in which semantic representation for each character string is stored. FIG. 5 is a diagram illustrated to describe an exemplary configuration of the natural language knowledge DB 124. As illustrated in FIG. 5, the natural language knowledge DB 124 has a character string 1240 and a semantic representation 1242 that are associated with each other. Here, a plurality of types of character strings (e.g., conversation sentences or the like) are recorded previously in the character string 1240. In addition, semantic representation corresponding to the associated character string is recorded in the semantic representation 1242. In one example, in the example illustrated in FIG. 5, "GO_RIGHT_SUBJECTIVE" is stored as the semantic representation corresponding to the character string "Go right!"

Moreover, as a modification, it is possible for the natural language processor 120 to convert the recognition result into the semantic representation using the known conversion technique as disclosed in, in one example, "*Spoken Language Understanding: Systems for Extracting Semantic Information from Voice*, by Gokhan Tur, Renato De Mori; Wiley (2011)".

{2-2-7. Disambiguation Unit 122}

The disambiguation unit 122, in a case where the semantic representation converted by the natural language processor 120 includes ambiguity, resolves the ambiguity of the semantic representation on the basis of the context information in collecting voice. In one example, the disambiguation unit 122 resolves the ambiguity of the semantic representation by referring to a disambiguation knowledge DB 126, which will be described later, on the basis of the semantic representation transferred from the natural language processor 120 and the context information in collecting voice.

(2-2-7-1. Context Information)

Here, in one example, the context information may include information indicating the positional relationship between the car 10 and the user in collecting voice. In one example, the context information indicates whether the user is located inside the car 10 or whether the user is located remotely of the car 10 in collecting voice. Further, in the case where the user is located outside the car 10, the context information indicates which of the front, rear, left, and right directions the user is located with respect to the car 10. Moreover, the context information is not limited to the four directions of the front, rear, left, and right, but more specified directions such as an oblique direction and a direction of 30 degrees from the right may be recorded.

In one example, in a case where the internal sound collector 100 collects voice, the context information may be generated in such a way to indicate that the user is located inside the car 10. In addition, in a case where the external sound collector 102 collects voice, the context information may be generated in such a way to indicate that the user is located outside the car 10 or indicate that the arrival direction and arrival time of the voice are included. In addition, in a case where voice is collected by the first remote sound collector 200 or the second remote sound collector 220, the context information may be generated in such a way to indicate that the user is located remotely of the car 10.

Further, the context information may include information regarding an image displayed on the display unit in collecting voice. In one example, in the case where voice is collected by the first remote sound collector 200, the context information may be generated in such a way to include information regarding an image displayed on the display unit of the HMD 20 in collecting voice (e.g., indicating that an image of which direction of the car 10 is displayed on the display unit, etc.). In addition, in the case where voice is collected by the second remote sound collector 220, the context information may be generated in such a way to include information regarding the display screen (e.g., a map screen, etc.) displayed on the display unit of the tablet terminal 22 in collecting voice. In one example, the context information includes information indicating the relationship between the display direction and the cardinal point of the map screen displayed on the display unit.

Alternatively, the context information may include a detection result related to the user's line of sight in collecting voice. In one example, the context information may be generated in such a way to include the line-of-sight direction of the user located outside the car 10, which is detected on the basis of image capture by a camera installed outside the car 10. Alternatively, the context information may be generated in such a way to include the line-of-sight direction of the user who is riding in it, which is detected on the basis of image capture by a camera installed inside the car 10.

(2-2-7-2. Disambiguation Knowledge DB 126)

The disambiguation knowledge DB 126 is a database in which a method of resolving the disambiguation for each semantic representation is stored. FIG. 6 is a diagram illustrated to describe an exemplary configuration of the disambiguation knowledge DB 126. As illustrated in FIG. 6, in the disambiguation knowledge DB 126, a semantic representation 1260, an internal sound collector 1262, an external sound collector 1264, a first remote sound collector 1266, and a second remote sound collector 1268 are associated with each other. Here, the semantic representation 1260 has a plurality of kinds of semantic representations with ambiguity recorded therein. In addition, the internal sound collector 1262, the external sound collector 1264, the first remote sound collector 1266, and the second remote sound collector 1268 have the respective interpretation methods corresponding to the relevant semantic representation recorded therein for the respective sound collectors (serving as a sender of transmission of the relevant voice).

Moreover, the interpretation method in the disambiguation knowledge DB 126 can be registered by, in one example, a user such as a car owner who performs initial setting. Alternatively, the interpretation method for each user can be registered in the disambiguation knowledge DB 126 by specifying the user (speaker) who performs the initial setting on the basis of an image or the like captured by the camera installed inside or outside the car 10.

Alternatively, contents of the disambiguation knowledge DB 126 may be automatically registrable. In one example, a user who requests registration is specified on the basis of an image or the like captured by a camera installed in the car 10, and the interpretation method obtained previously by machine learning in association with attribute information of the relevant user (e.g., age, sex, etc.) can be automatically registered in the disambiguation knowledge DB 126.

(2-2-7-3. Interpretation Example 1)

In Collecting Voice by Internal Sound Collector 100

The interpretation method performed by the disambiguation unit 122 for the semantic representation "GO_RIGHT_SUBJECTIVE" illustrated in FIG. 6 is now described in detail. In one example, in a case where the internal sound collector 100 collects a voice ("Go right"!), the disambiguation unit 122 interprets the semantic representation as "GO_RIGHT", that is, a command to make the car 10 turn right.

In Collecting Voice by External Sound Collector 102

Further, in a case where the external sound collector 102 collects the voice, the disambiguation unit 122 interprets the semantic representation in such a way to move the car 10 to the right using the front direction of the user as a reference. Specifically, the disambiguation unit 122 interprets the semantic representation on the basis of the arrival direction of the voice in collecting voice.

Figure 7A:
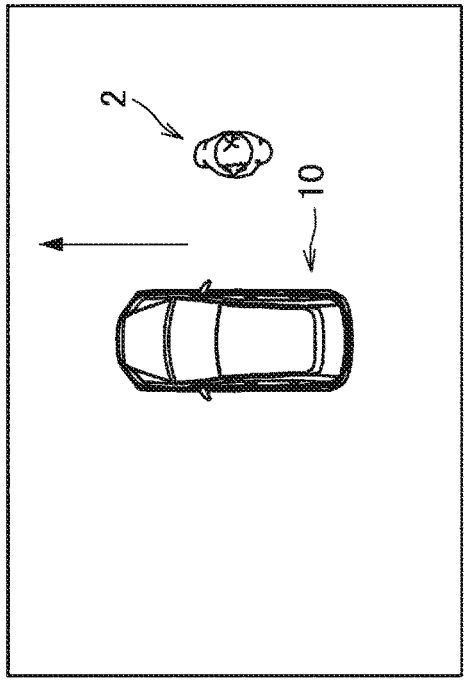
FIGS. 7A, 7B, 7C, and 7D are diagrams illustrated to describe an example of semantic interpretation of voice in a case where "Go right!" is uttered from the outside of the car 10.
Figure 7B:
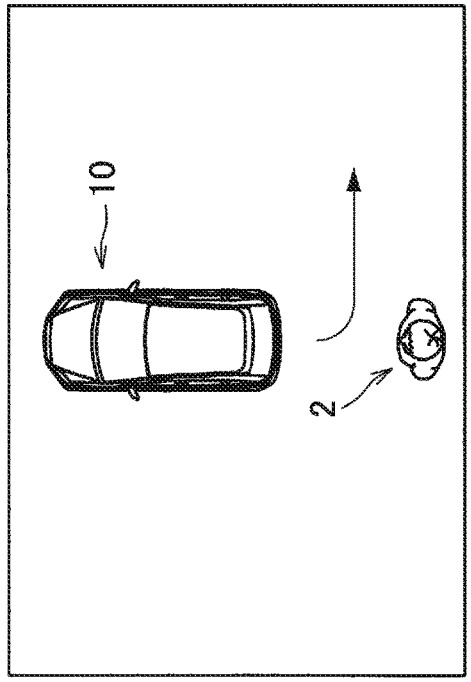
Figure 7C:
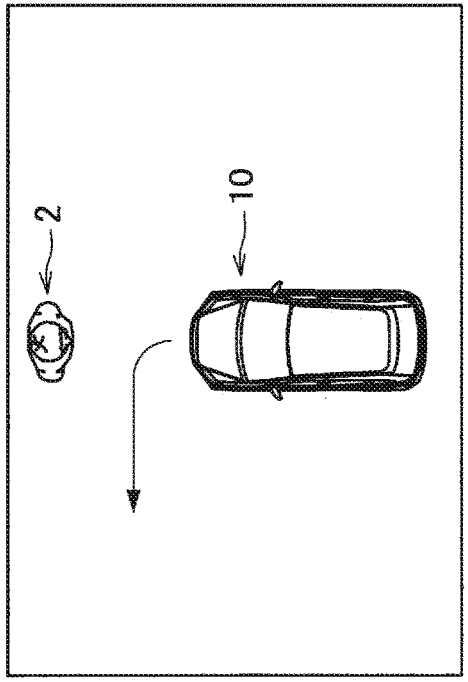
Figure 7D:
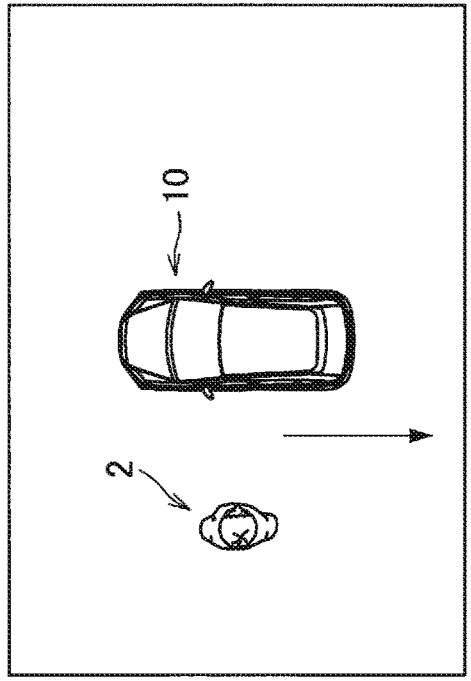

The function described above is now described in more detail with reference to FIGS. 7A, 7B, 7C, and 7D. FIGS. 7A, 7B, 7C, and 7D are diagrams illustrated to describe, in the case where the user utters a voice "Go right!" from each of the front, rear, left, and right directions of the car 10, a method of interpreting the meaning of the voice. In one example, as illustrated in FIG. 7A, in a case where the voice arrives from the front of the car 10 (FRONT_VOICE), the disambiguation unit 122 interprets the relevant semantic representation as "GO_LEFT", that is, a command to make the car 10 turn left as illustrated in FIG. 6. Further, as illustrated in FIG. 7B, in a case where the voice arrives from the right of the car 10 (RIGHT_VOICE), the disambiguation unit 122 interprets the semantic representation as "GO_FRONT", that is, a command to move the car 10 forward as illustrated in FIG. 6. In addition, as illustrated in FIG. 7C, in a case where the voice arrives from the left of the car 10 (LEFT_VOICE), the disambiguation unit 122 interprets the semantic representation as "BACK_FORWARD", that is, a command to move the car 10 backward as illustrated in FIG. 6. As illustrated in FIG. 7D, in a case where the voice arrives from behind the car 10, the disambiguation unit 122 interprets the semantic representation as "BACK_RIGHT", that is, a command to make the car 10 turn right while reversing, as illustrated in FIG. 6.

In Collecting Voice by First Remote Sound Collector 200

Further, in a case where the voice is collected by the first remote sound collector 200 (the HMD 20), the disambiguation unit 122 interprets the semantic representation on the basis of an image displayed on the display unit of the HMD 20 in collecting voice. In one example, in a case where an image obtained by capturing the front of the car 10 is displayed on the HMD 20 (FRONTVIEW) in collecting the voice, the disambiguation unit 122 interprets the semantic representation as "GO_RIGHT", that is, a command to make the car 10 turn right, as illustrated in FIG. 6. In addition, in a case where an image obtained by capturing the rear of the car 10 is displayed on the HMD 20 in collecting the voice, the disambiguation unit 122 interprets the semantic representation as "BACK_LEFT", that is, a command to make the car 10 turn left while reversing, as illustrated in FIG. 6.

In Collecting Voice by Second Remote Sound Collector 220

Further, in a case where the voice is collected by the second remote sound collector 220 (the tablet terminal 22), the disambiguation unit 122 interprets the semantic representation on the basis of a screen displayed on the display unit of the tablet terminal 22 in collecting voice. In one example, the disambiguation unit 122 interprets the semantic representation on the basis of the relationship between the display direction and cardinal point of the map screen displayed on the display unit of the tablet terminal 22 in collecting voice.

Figure 8:
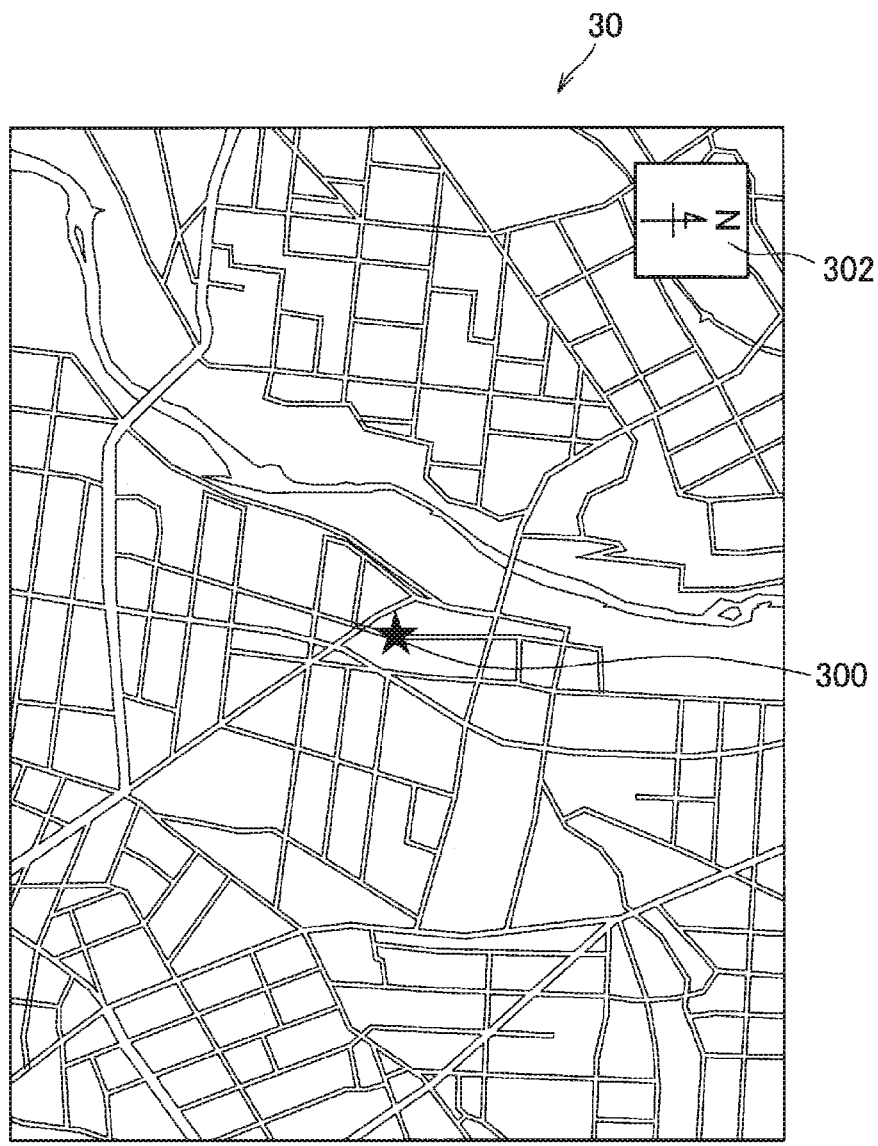
FIG. 8 is a diagram illustrated to describe a display example of a map screen according to the first embodiment.

The function described above is now described in more detail with reference to FIG. 8. FIG. 8 is a diagram illustrated to describe a display example of a map screen (a map screen 30). Moreover, FIG. 8 illustrates an example in which the upper side of the map screen 30 is displayed in a display orientation that it faces the "west". In addition, a position 300 indicates the current position of the car 10 on the map screen 30.

In one example, in a case where the map screen 30 is displayed on the display unit of the tablet terminal 22 in collecting the voice, the disambiguation unit 122 interprets the relevant semantic representation as "GO_DIR (MAP_RIGHT)", that is, a command to move the car 10 to the cardinal point corresponding to the right direction on the map screen 30 ("north" in the example illustrated in FIG. 8).

(2-2-7-4. Interpretation Example 2)

Meanwhile, it is also assumed that the user's voice is collected by a plurality of sound collectors. In one example, in a case where the user's voice is collected by the internal sound collector 100 and the external sound collector 102, the disambiguation unit 122 is capable of interpreting the semantic representation corresponding to the voice using the interpretation method corresponding to one of the internal sound collector 100 and the external sound collector 102. In one example, the disambiguation unit 122 may interpret the semantic representation using the interpretation method corresponding to the sound collector having larger magnitude of the collected voice of the internal sound collector 100 and the external sound collector 102. Alternatively, the disambiguation unit 122 may interpret the semantic representation using the interpretation method corresponding to the sound collector of which the arrival time of the voice is earlier of the internal sound collector 100 and the external sound collector 102.

Further, it is also assumed that the tablet terminal 22 is located inside the car 10 and the user's voice is collected by the internal sound collector 100 and the tablet terminal 22 (the second remote sound collector 220). In this case, the disambiguation unit 122 may interpret the semantic representation corresponding to the relevant voice on the basis of whether it is estimated that the tablet terminal 22 is operated in collecting voice. In one example, in a case where it is estimated that the tablet terminal 22 is being operated in collecting voice, the disambiguation unit 122 interprets the semantic representation using the interpretation method corresponding to the tablet terminal 22. In addition, in a case where it is estimated that the tablet terminal 22 is not being operated in collecting voice, the disambiguation unit 122 interprets the semantic representation using the interpretation method corresponding to the internal sound collector 100.

Moreover, whether the user operates the tablet terminal 22 can be estimated on the basis of a measurement result obtained by the tablet terminal 22. In one example, in a case where movement of the tablet terminal 22 is detected by an accelerometer of the tablet terminal 22 or where the user's holding of the tablet terminal 22 (inclination of the tablet terminal 22) is detected by a gyroscope of the tablet terminal 22, it is estimated that the user is operating the tablet terminal 22.

(2-2-7-5. Modification 1)

Moreover, in a modification, the disambiguation unit 122 is also capable of resolving the ambiguity of the semantic representation corresponding to the collected voice on the basis of an image in which the user is estimated to view in collecting voice. In one example, in a case where the user is located inside the car 10 and the voice "Go right!" is collected by the internal sound collector 100, the disambiguation unit 122 is capable of resolving the ambiguity of the semantic representation corresponding to the relevant voice on the basis of the user's line-of-sight direction specified from the image captured by the camera installed inside the car 10.

More specifically, in a case where it is specified that the user's line-of-sight direction in collecting voice is in front of the car 10, the disambiguation unit 122 is capable of interpreting the semantic representation as a command to make the car 10 turn right. In addition, in a case where it is specified that the user's line-of-sight direction in collecting voice is the rear of the car 10, the disambiguation unit 122 is capable of interpreting the semantic representation as a command to make the car 10 turn left while reversing. In addition, in a case where it is specified that the user's line-of-sight direction in collecting voice is the right direction of the car 10, the disambiguation unit 122 is capable of interpreting the semantic representation as a command to move the car 10 backward. In addition, in a case where it is specified that the user's line-of-sight direction in collecting voice is the left direction of the car 10, the disambiguation unit 122 is capable of interpreting the semantic representation as a command to move the car 10 forward.

Figure 9A:
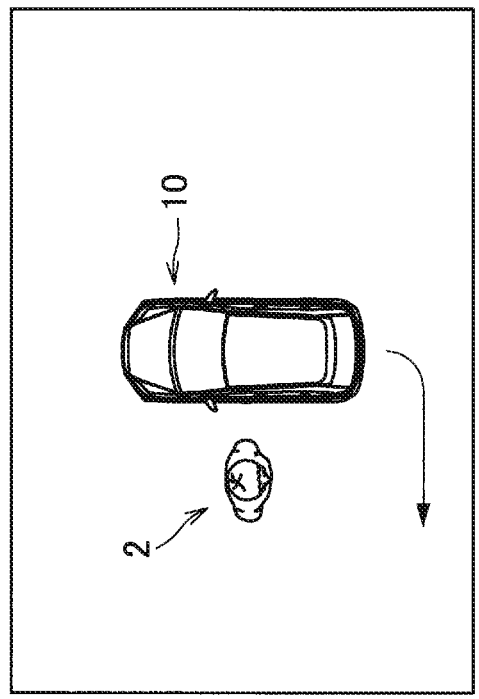
FIGS. 9A and 9B are diagrams illustrated to describe a modification of the semantic interpretation of voice in the case where "Go right!" is uttered from outside the car 10.
Figure 9B:
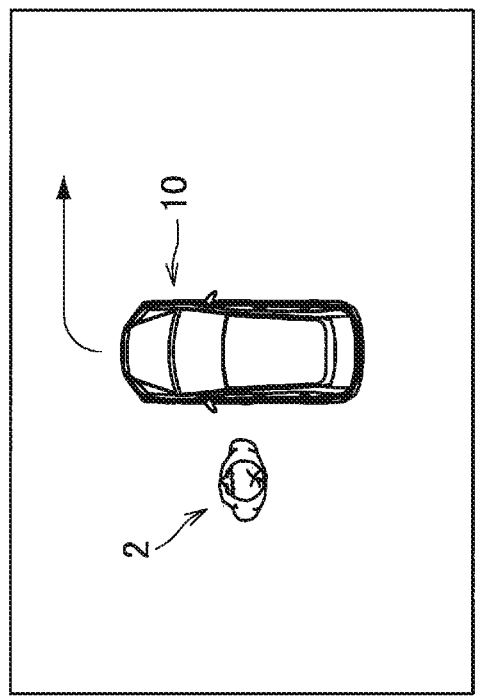

Further, in a case where the user is located outside the car 10 and the voice "Go right!" is collected by the external sound collector 102, the disambiguation unit 122 is also capable of resolving the ambiguity of the semantic representation corresponding to the voice on the basis of the user's line-of-sight direction specified from the image captured by the camera installed outside the car 10. The function described above is now described in more detail with reference to FIGS. 9A and 9B. In one example, as illustrated in FIG. 9A, in a case where the user is located on the left side of the car 10 and it is specified that the user's line-of-sight direction in collecting voice is in front of the car 10, the disambiguation unit 122 is capable of interpreting the semantic representation as a command to make the car 10 turn right. In addition, as illustrated in FIG. 9B, in a case where the user is located on the left side of the car 10 and it is specified that the user's line-of-sight direction in collecting voice is behind the car 10, the disambiguation unit 122 is capable of interpreting the semantic representation as a command to make the car 10 turn left while reversing. According to this interpretation example, it is possible to switch appropriately the semantic interpretation of the voice recognition result depending on the direction in which the user views at the time of uttering the command even if the user is located at the same place.

(2-2-7-6. Modification 2)

Moreover, the example of the disambiguation knowledge DB 126 illustrated in FIG. 6 shows the interpretation method for causing the user to move the car 10 to the right in the case where the voice "Go right!" is collected by the external sound collector 102, but it is not limited to such an example. In one example, in the case where the voice "Go right!" is collected by the external sound collector 102, the disambiguation knowledge DB 126 may be registered such that the car 10 is typically caused to be moved to the right. In addition, the interpretation methods corresponding to the respective semantic representations may be switchable depending on user's preference.

{2-2-8. Controller 110}

The controller 110 generates a control command on the basis of the semantic interpretation result obtained by the semantic interpretation unit 108. In one example, the controller 110 generates a control command regarding the movement of the car 10. In addition, the controller 110 transfers the generated control command to the driving unit 112.

{2-2-9. Driving Unit 112}

The driving unit 112 drives, in one example, an engine or the like in accordance with the control command transferred from the controller 110.

Moreover, the configuration of the car 10 according to the first embodiment is not limited to the example described above. In one example, the internal sound collector 100 or the external sound collector 102 may not necessarily be fixed to the car 10. In addition, in one example, the voice recognizer 106, the semantic interpretation unit 108, and the controller 110 may be provided in a server (not shown) connected to the communication network 24. Then, in this modification, the server may be the information processing apparatus according to the present disclosure. In addition, the car 10 is capable of acquiring a control command corresponding to the voice of a command issued by the user from the server via the communication network 24.

<2-3. Operation>

The configuration according to the first embodiment is described above. An example of the operation according to the first embodiment is now described with reference to FIG. 10.

Figure 10:
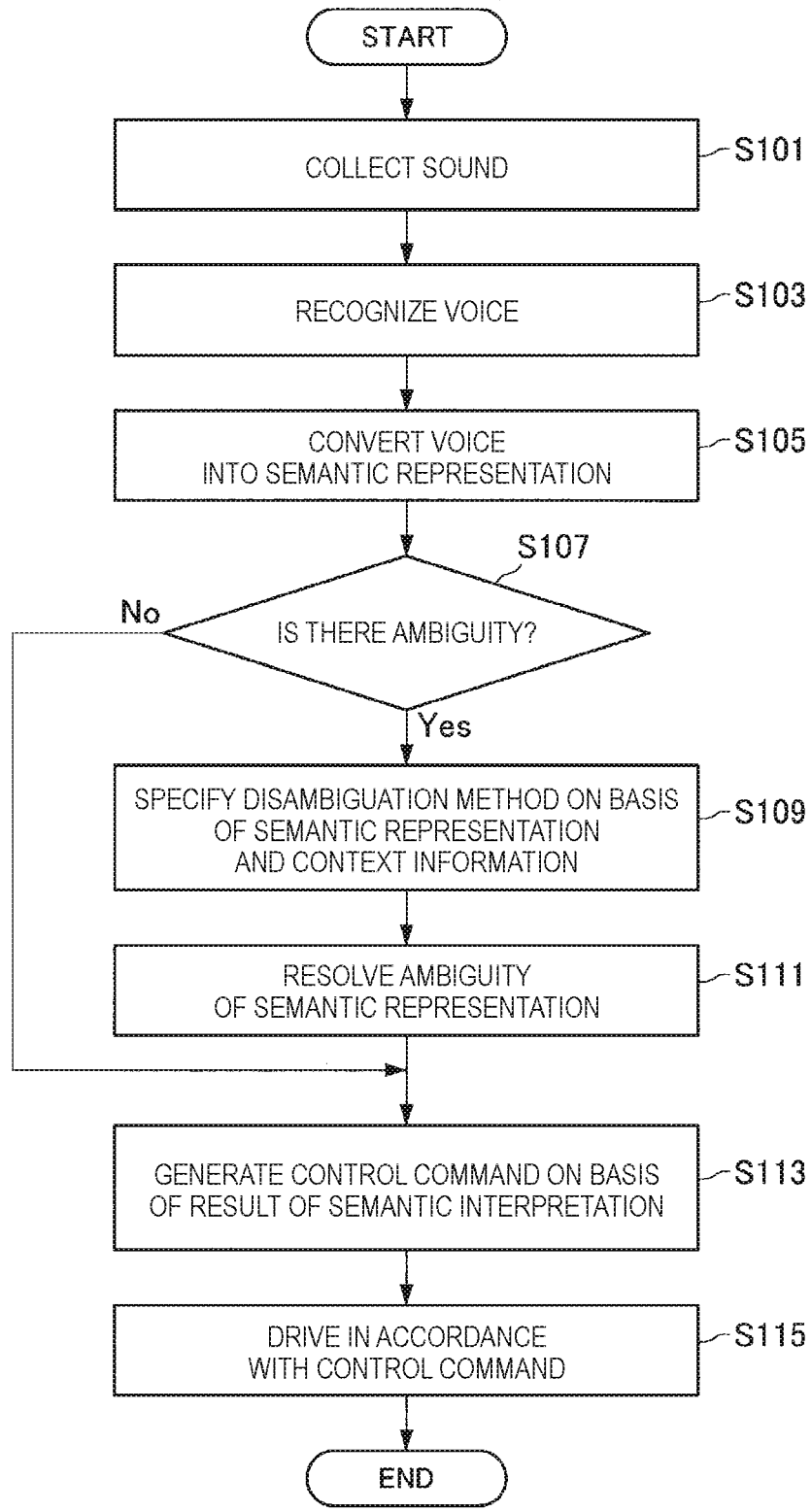
FIG. 10 is a flowchart illustrating an operation example according to the first embodiment.

As illustrated in FIG. 10, the voice uttered by the user is first collected by any one of the internal sound collector 100, the external sound collector 102, the first remote sound collector 200, and the second remote sound collector 220. Then, the relevant sound collector transfers the collected voice and the context information in collecting voice to the voice recognizer 106 (S101).

Subsequently, the voice recognizer 106 recognizes the voice transferred in S101 (S103). Then, the semantic interpretation unit 108 (the natural language processor 120) converts the voice recognition result into a semantic representation by referring to the natural language knowledge DB 124 (S105).

Subsequently, the semantic interpretation unit 108 (the disambiguation unit 122) determines whether the converted semantic representation includes ambiguity (S107). If there is no ambiguity (No in S107), the car 10 performs processing of S113 described later.

On the other hand, if there is ambiguity (Yes in S107), the semantic interpretation unit 108 refers to the disambiguation knowledge DB 126 on the basis of the semantic representation converted in S105 and the context information acquired in S101, and specifies a method of resolving the ambiguity of the semantic representation (S109).

Then, the semantic interpretation unit 108 resolves the ambiguity of the semantic representation using the specified resolution method (S111).

Subsequently, the controller 110 generates a control command on the basis of the result of the semantic interpretation in S105 or S111 (S113).

Then, the driving unit 112 drives an engine or the like in accordance with the generated control command (S115).

<2-4. Effect>

According to the first embodiment as described above, in the case where a command is uttered to the car 10, the car 10 interprets the meaning of the command on the basis of the voice recognition result and the context information in collecting voice. Thus, it is possible to properly interpret the meaning of the command depending on the situation in which the command is uttered.

In one example, in the case where the semantic representation corresponding to the voice recognition result includes ambiguity, the car 10 resolves the ambiguity of the semantic representation, in one example, on the basis of the positional relationship between the car 10 and the user in collecting voice or contents of an image displayed on the HMD 20 or the tablet terminal 22. Thus, in one example, even in a case where a command including direction-related ambiguity is uttered, the car 10 is capable of being moved by interpreting the meaning of the command in such a way to follow the intuition of the user (utterer).

«3. Second Embodiment»

<3-1. Overview>

Figure 11:
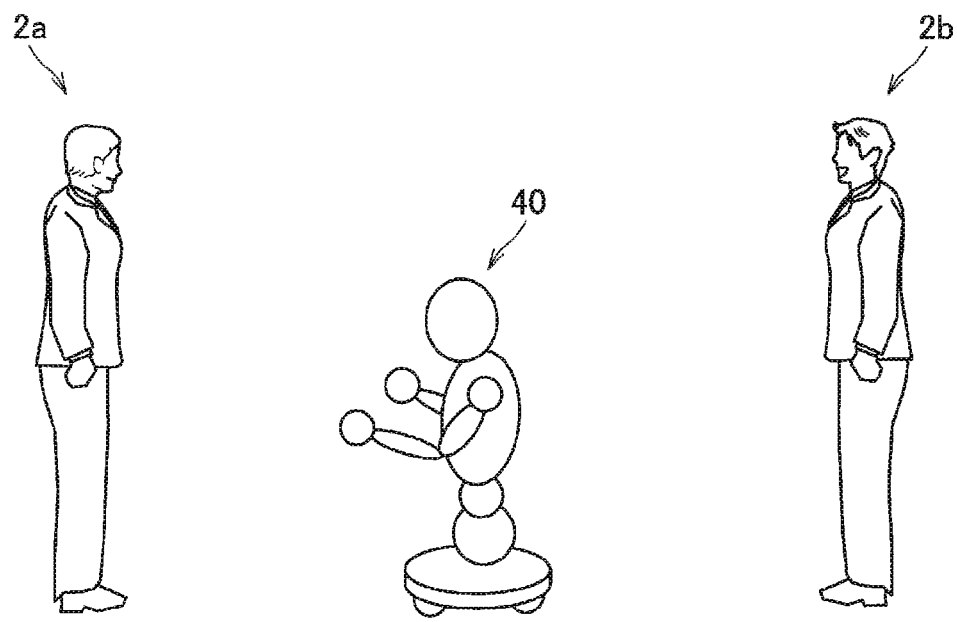
FIG. 11 is a diagram illustrated to describe how one of two users gives a command by voice to a robot 40, according to a second embodiment.

The first embodiment is described above. A second embodiment is now described. FIG. 11 is a diagram illustrated to describe an overview of the second embodiment. As illustrated in FIG. 11, in the second embodiment, in one example, it is assumed that two users 2 are positioned with the robot 40 interposed therebetween and only the user 2b utters a command to the robot 40. In one example, the user 2b instructs the robot 40 to move by the voice "Come on!"

Meanwhile, the command "Come on!" is a command to bring the robot 40 closer to the user who utters the voice, and so the robot 40 is first necessary to specify which one of the two users uttering the voice.

As will be described later, in a case where a command is uttered from any one of a plurality of users, the robot 40 according to the second embodiment is capable of specifying the user who utters the voice. Furthermore, the robot 40 is capable of appropriately interpreting the meaning of the recognition result on the basis of the specified user and the voice recognition result. Moreover, the robot 40 is an example of the information processing apparatus and the device according to the present disclosure.

<3-2. Configuration>

Figure 12:
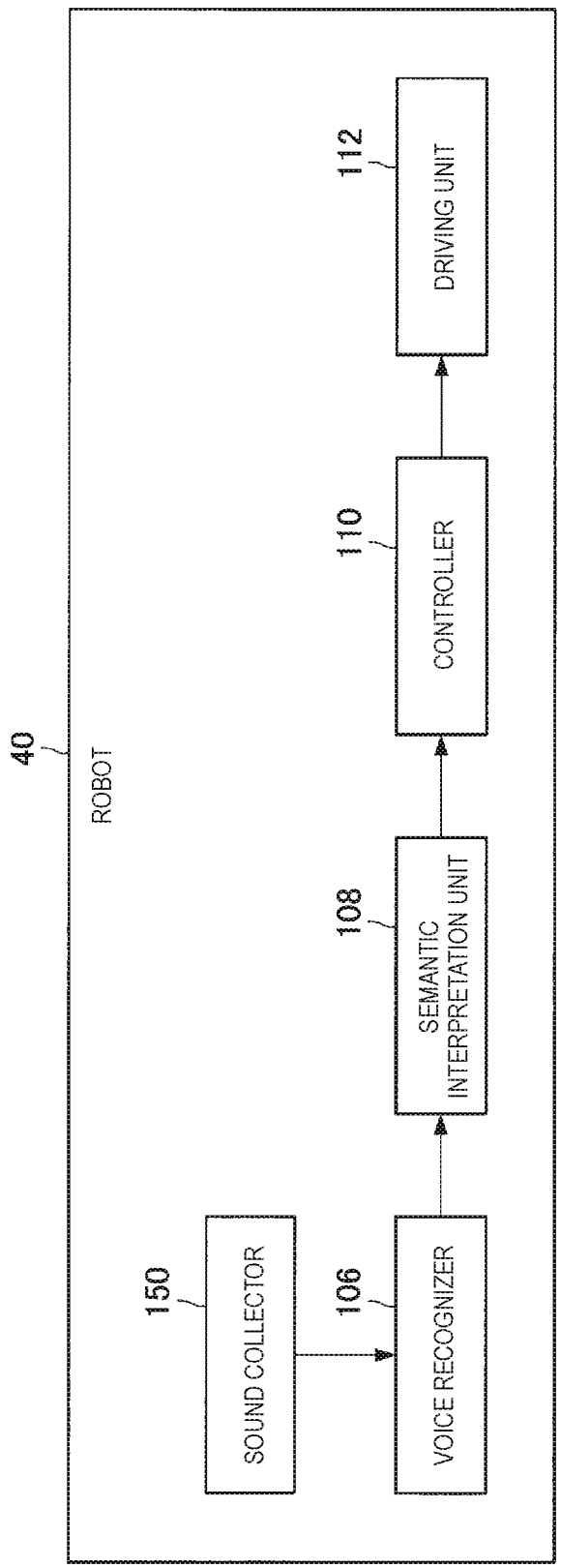
FIG. 12 is a functional block diagram illustrating an exemplary configuration of the robot 40 according to the second embodiment.

The configuration according to the second embodiment is now described in more detail. FIG. 12 is a functional block diagram illustrating an exemplary configuration of the robot 40 according to the second embodiment. As illustrated in FIG. 12, the robot 40 includes a sound collector 150, a voice recognizer 106, a semantic interpretation unit 108, a controller 110, and a driving unit 112. Moreover, in the following description, only components having functions different from those of the first embodiment will be described.

{3-2-1. Sound Collector 150}

The sound collector 150 detects sound outside the robot 40 and converts it into an electrical signal. In addition, the sound collector 150 transfers the collected voice and context information in collecting voice (e.g., information indicating the arrival direction of the voice, etc.) to the voice recognizer 106.

{3-2-2. Semantic Interpretation Unit 108}

The semantic interpretation unit 108 according to the second embodiment includes a natural language processor 120 and a disambiguation unit 122, as illustrated in FIG. 4, which is similar to the first embodiment.

{3-2-3. Disambiguation Unit 122}

In the case where the semantic representation converted by the natural language processor 120 includes ambiguity, the disambiguation unit 122 according to the second embodiment resolves the ambiguity of the semantic representation on the basis of the context information in collecting voice. In one example, in the case where the voice "Come on!" is collected, the disambiguation unit 122 interprets the semantic representation as a command to move it near the user by using a result obtained by specifying the user on the basis of the arrival direction of the voice.

Moreover, the user who utters the voice can be specified as follows. In one example, when utterance of voice is detected, the robot 40 first points a camera (not shown) installed in the robot 40 in the direction in which the voice arrived, and then captures an image. Then, the robot 40 determines whether the user located in the direction that points the camera is the user who utters the voice on the basis of the captured image. In one example, the robot 40 checks whether the face of the user faces the robot 40, thereby determining whether the user is the user who utters the voice. Moreover, the determination of whether the face of the user faces the direction of the robot 40 can be performed on the basis of the distance between the black eyes of the captured user, or can be performed on the basis of a result of the machine learning of the whole face.

Furthermore, the robot 40 analyzes whether the user is uttering on the basis of the image of the captured user's face or mouth, thereby determining whether the captured user is the user who utters the voice. Moreover, in a case where the voice and face for each user are registered previously, the robot 40 identifies the captured face and the collected voice, so the robot 40 is capable of specifying the identity of the user who utters the voice. Alternatively, in a case where attribute (sex, age, etc.) of each user is registered previously, the robot 40 estimates the attribute of the captured user on the basis of the identification of the captured face or estimates the attribute of the user on the basis of the identification of the collected voice, thereby specifying the identity of the user.

{3-2-4. Controller 110}

The controller 110 according to the second embodiment generates a control command for performing, in one example, control to move the robot 40, on the basis of the result of semantic interpretation by the semantic interpretation unit 108.

{3-2-5. Driving Unit 112}

The driving unit 112 according to the second embodiment moves the robot 40 in accordance with the control command transferred from the controller 110.

<3-3. Effect>

According to the second embodiment as described above, in the case where a command is uttered from any one of a plurality of users, the robot 40 is capable of specifying the identity of the user who utters the voice on the basis of the context information in collecting voice. Then, the robot 40 interprets the meaning of the recognition result of the voice on the basis of the specified user. For this reason, in one example, even if the robot 40 is positioned between two users and the command "Come on!" is uttered by one of the users, the robot 40 is capable of appropriately approaching the user who utters the voice.

«4. Third Embodiment»

The second embodiment is described above. A third embodiment is now described. As described later, according to the third embodiment, in a case where a command is uttered by a doctor in a camera system for endoscopic surgery, it is possible to properly interpret the meaning of the command on the basis of the recognition result of the voice and the context information in collecting voice. This makes it possible to interpret properly the meaning of the command in such a way to follow the intuition of the doctor depending on the situation in which the command is uttered.

<4-1. Configuration of Information Processing System>

Figure 13:
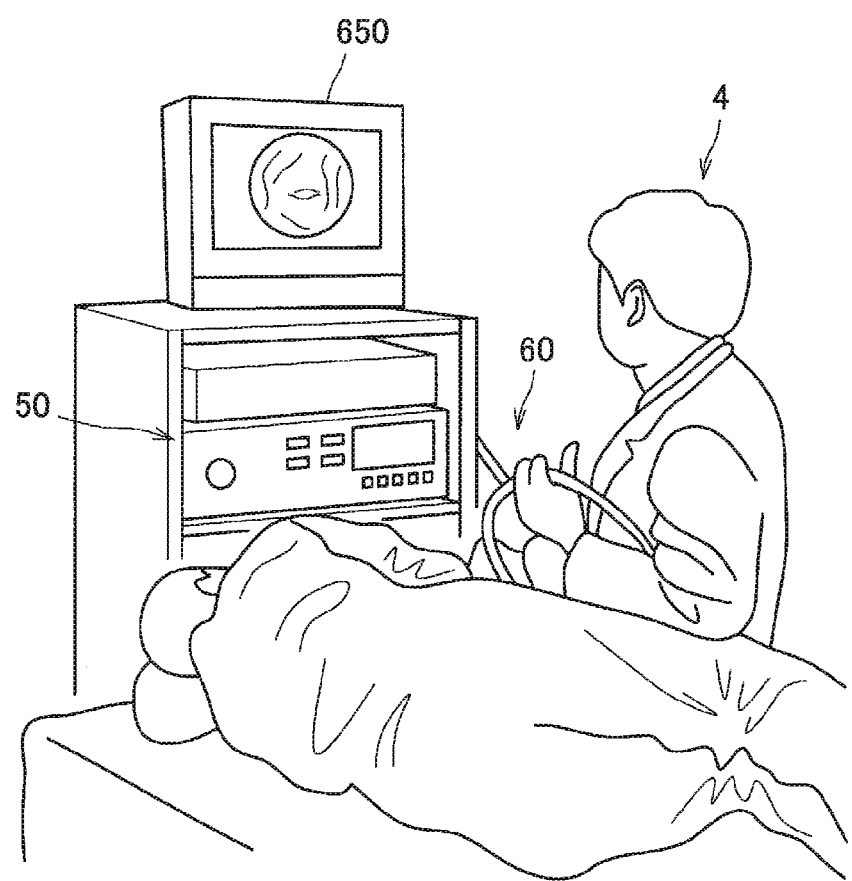
FIG. 13 is a diagram illustrated to describe an exemplary configuration of an information processing system according to a third embodiment.

FIG. 13 is a diagram illustrated to describe an exemplary configuration of an information processing system according to the third embodiment. As illustrated in FIG. 13, the information processing system according to the third embodiment includes an information processing apparatus 50 and an endoscope 60.

{4-1-1. Information Processing Apparatus 50}

The information processing apparatus 50 is an apparatus for controlling the operation of the endoscope 60. In one example, the information processing apparatus 50 controls zooming of the endoscope 60 (an imaging unit 604 of the endoscope 60) and vertical movement of the visual field. In addition, the information processing apparatus 50 changes the imaging range captured by the endoscope 60 and adjusts the range of light irradiated by the endoscope 60.

{4-1-2. Endoscope 60}

The endoscope 60 is an instrument for capturing an image inside the patient's body. The endoscope 60 has an imaging unit 604 that performs imaging and an illumination unit 606 for illuminating the imaging range. In one example, the endoscope 60 displays a part of the captured images on a display unit 650. Then, the user (doctor) is capable of checking the result captured by the endoscope 60 by viewing the image displayed on the display unit 650. Moreover, the orientation (display direction) in which the captured image is displayed on the display unit 650 can be optionally changed by the user.

Further, the endoscope 60 is capable of changing the position and attitude of the imaging unit 604 and the illumination unit 606 on the basis of the control information received from the information processing apparatus 50.

<4-2. Configuration>

Figure 14:
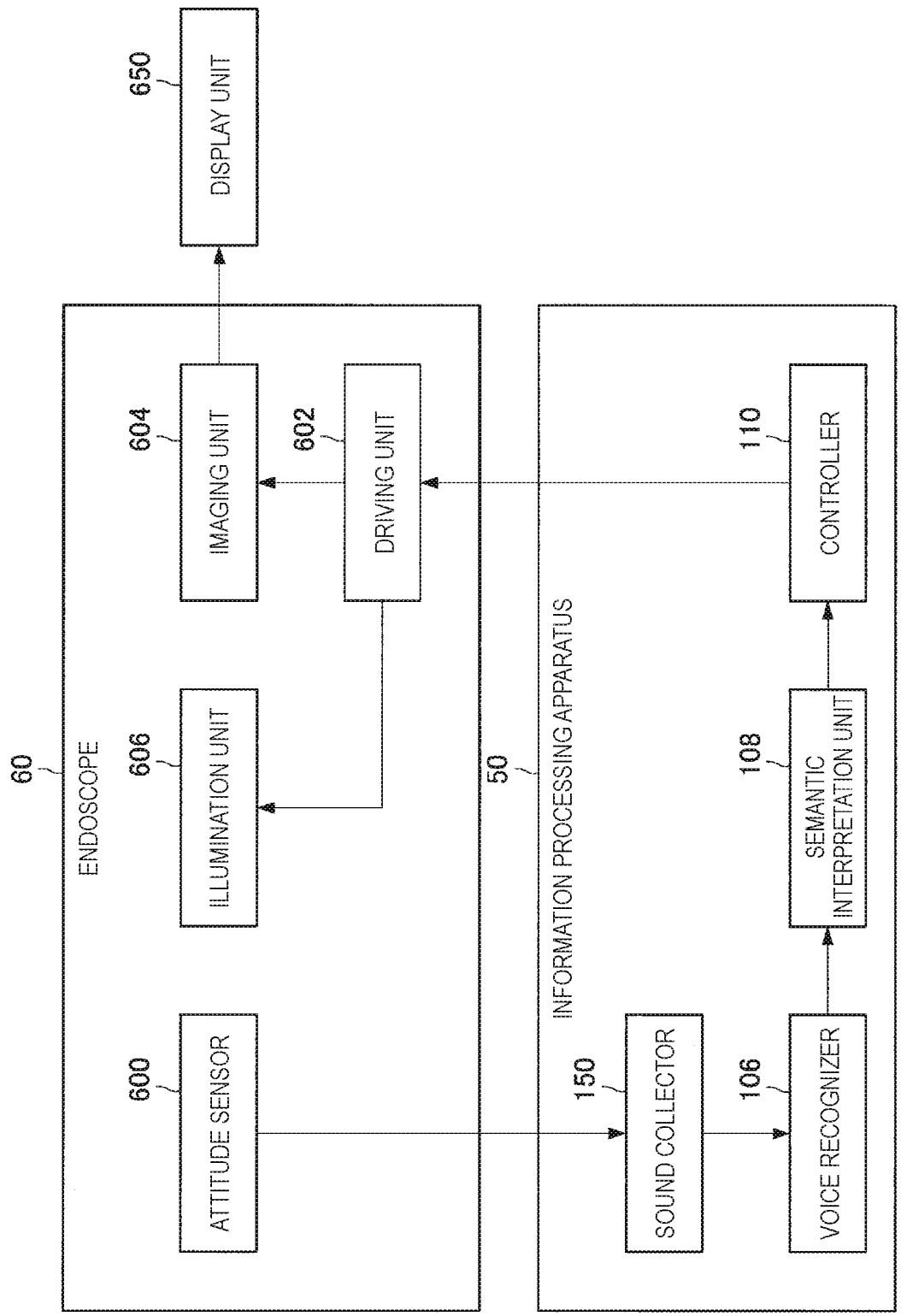
FIG. 14 is a functional block diagram illustrating an exemplary configuration of an information processing apparatus 50 and an endoscope 60 according to the third embodiment.

The configuration of the information processing system according to the third embodiment is described above. The configuration according to the third embodiment is now described in detail. FIG. 14 is a functional block diagram illustrating an exemplary configuration of the endoscope 60 and the information processing apparatus 50 according to the third embodiment. Moreover, in the following description, only components having functions different from those of the first embodiment or the second embodiment will be described.

{4-2-1. Endoscope 60}

The configuration of the endoscope 60 is now described. As illustrated in FIG. 14, the endoscope 60 includes an attitude sensor 600, a driving unit 602, an imaging unit 604, and an illumination unit 606.

(4-2-1-1. Attitude Sensor 600)

The attitude sensor 600 is a sensor for detecting attitude information of the imaging unit 604 and the illumination unit 606. In addition, the attitude sensor 600 sequentially transmits the detected attitude information of the imaging unit 604 and the detected attitude information of the illumination unit 606 to the information processing apparatus 50.

(4-2-1-2. Driving Unit 602)

The driving unit 602 changes or shifts the attitude of the imaging unit 604 or the illumination unit 606, in one example, on the basis of the control information received from the information processing apparatus 50.

(4-2-1-3. Imaging Unit 604)

The imaging unit 604 captures an external image. In one example, the imaging unit 604 shifts the imaging range or changes the zoom magnification under the control of the driving unit 602. In addition, the endoscope 60 may have only one imaging unit 604 or two or more imaging units 604.

(4-2-1-4. Illumination Unit 606)

The illumination unit 606 irradiates light such as white light. The illumination unit 606 is constituted as an LED, a lamp, or the like. Moreover, the endoscope 60 may have only one illumination unit 606 or two or more illumination units 606. Moreover, it is assumed that the imaging unit 604 and the illumination unit 606 are configured as mutually independent devices (operation devices).

{4-2-2. Information Processing Apparatus 50}

The configuration of the information processing apparatus 50 is now described. As illustrated in FIG. 14, the information processing apparatus 50 includes a sound collector 150, a voice recognizer 106, a semantic interpretation unit 108, and a controller 110.

(4-2-2-1. Sound Collector 150)

The sound collector 150 according to the third embodiment detects sound outside the information processing apparatus 50 and converts it into an electrical signal. In addition, the sound collector 150 transfers the collected voice and the context information in collecting voice (e.g., information regarding the orientation (display direction) in which the captured image is displayed on the display unit 650 and attitude information of the imaging unit 604 or attitude information of the illumination unit 606 which are received from the endoscope 60, etc.) to the voice recognizer 106.

(4-2-2-2. Disambiguation Unit 122)

Resolution Example 1

In a case where the semantic representation converted by the natural language processor 120 includes ambiguity, the disambiguation unit 122 according to the third embodiment resolves the ambiguity of the semantic representation on the basis of the context information in collecting voice. In one example, in a case where the display direction of the captured image displayed on the display unit 650 is switchable and the voice including the direction-related ambiguity, such as "Show me the right!" or "Zoom on the right", is recognized, the disambiguation unit 122 interprets the semantic representation corresponding to the recognition result as a command to change the imaging direction of the imaging unit 604 on the basis of the information regarding the display direction of the captured image on the display unit 650. In one example, in the case where the voice "Show me the right!" is recognized, the disambiguation unit 122 interprets the semantic representation as a command to change the imaging direction of the imaging unit 604 in such a way that the area on the right side of the image displayed on the display unit 650 is displayed at a position closer to the center on the display unit 650.

Figure 15:
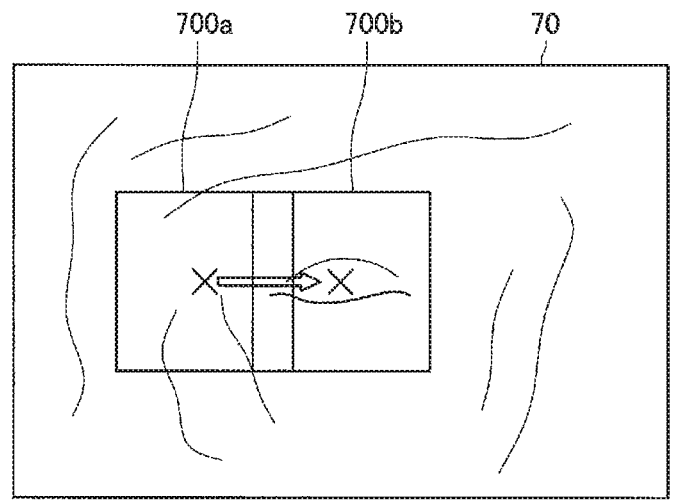
FIG. 15 is a diagram illustrated to describe an example of the semantic interpretation of voice in a case where "Show me the right!" is uttered.

FIG. 15 is a diagram illustrated to describe an exemplary image (a captured image 70) captured by the imaging unit 604. Moreover, the captured image 70 indicates the entire image captured by an image sensor included in the imaging unit 604. In addition, a display area 700 illustrated in FIG. 15 indicates an image area displayed on the display unit 650 in the captured image 70. In one example, in the case where the display area 700a is displayed on the display unit 650 and the voice "Show me the right!" is collected, the disambiguation unit 122 interprets it as a command to move the display area 700 in a direction corresponding to the right direction (display direction) in the image displayed on the display unit 650.

Resolution Example 2

Further, in a case where the imaging unit 604 and the illumination unit 606 exist independently and the voice including ambiguity regarding the direction of illumination such as "Shift the light to the right!" is recognized, the disambiguation unit 122 interprets the semantic representation corresponding to the recognition result as a command to change the attitude of the illumination unit 606 on the basis of the information regarding the display direction of the captured image in the display unit 650, the attitude information of the image capturing unit 604, and the attitude information of the illumination unit 606.

Figure 16:
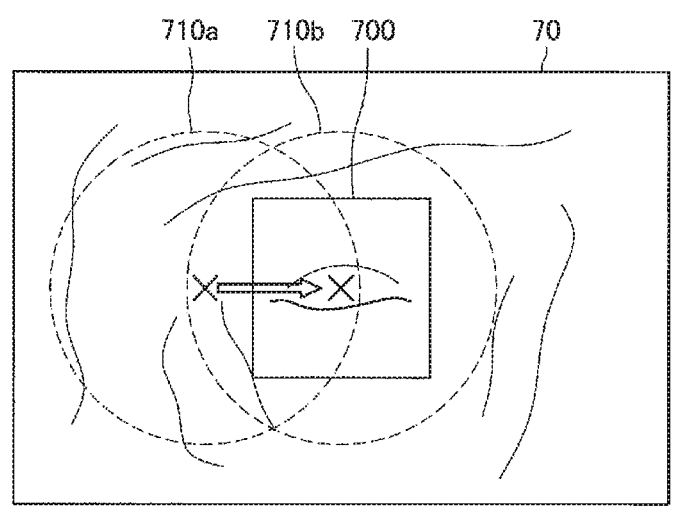
FIG. 16 is a diagram illustrated to describe an example of the semantic interpretation of voice in a case where "Shift the light right!" is uttered.

FIG. 16 is a diagram illustrated to describe an irradiation range 710, which is the range irradiated by the illumination unit 606 in the patient's body, together with the captured image 70. In one example, in a case where the range currently irradiated by the illumination unit 606 is the irradiation range 710a and the voice "Shift the light to the right!" is collected, the disambiguation unit 122 interprets the semantic representation corresponding to the voice as a command to move the irradiation range 710 in the direction corresponding to the right direction (display direction) in the image displayed on the display unit 650.

Modification

Moreover, as a modification, in a case where an image obtained by combining images captured by each of the two imaging units 604 is displayed on the display unit 650 and voice "show me the right!" is collected, the disambiguation unit 122 is capable of interpreting the meaning of the voice as a command to cause the display unit 650 to display an image captured by only the imaging unit 604 corresponding to the right direction in the image displayed on the display unit 650.

(4-2-2-3. Controller 110)

The controller 110 according to the third embodiment generates a control command directed to the endoscope 60 on the basis of the result of the semantic interpretation by the semantic interpretation unit 108. In addition, the controller 110 transmits the generated control command to the endoscope 60 (the driving unit 602).

<4-3. Effect>

According to the third embodiment as described above, in a case where a doctor utters a command, the information processing apparatus 50 interprets the meaning of the command on the basis of the voice recognition result and the context information in collecting voice. In one example, in the case where the voice "Show me the right!" is collected, the information processing apparatus 50 interprets the meaning of the recognition result as a command to change the imaging direction of the imaging unit 604 on the basis of information regarding the display direction of the image (i.e., the image viewed by the doctor) displayed on the display unit 650. Thus, it is possible to properly interpret the meaning of the command in such a way to follow the intuition of the doctor.

<4-4. Modification>

Moreover, although the above description is given of the example in which the third embodiment is applied to a camera system for endoscopic surgery, the third embodiment is not limited to this example. In one example, the third embodiment is also applicable to a case where a microscope and the information processing apparatus 50 are connected to each other and the user employs the microscope. In one example, in the case where a part of images captured by the microscope is displayed on the display unit and a command including ambiguity such as "Show me the right!" or "Zoom on the right!" is uttered by the user, the information processing apparatus 50 is capable of interpreting the meaning of the command using an interpretation method similar to that described above.

«5. Fourth Embodiment»

<5-1. Overview>

Figure 17:
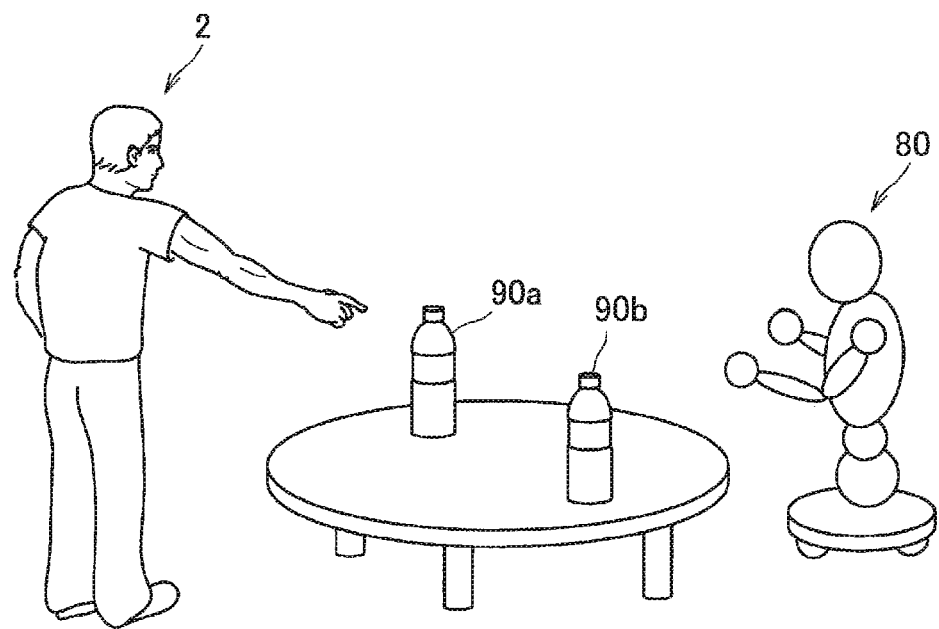
FIG. 17 is a diagram illustrated to describe how to give a command by voice to a robot 80 according to a fourth embodiment.

The third embodiment is described above. A fourth embodiment is now described. FIG. 17 is a diagram illustrated to describe the overview of the fourth embodiment. In the fourth embodiment, it is assumed that a case where a user instructs a robot 80 to perform a voice operation (e.g., carrying an object) related to any one object in a scene where a plurality of objects are present. In one example, as illustrated in FIG. 17, a plurality of PET bottles 90 are placed within a range that can be detected by the robot 80, and the user 2 instructs the robot 80 to grasp one of the PET bottles 90 through voice such as "Take PET bottle!"

Meanwhile, it is ambiguous which one of the plurality of PET bottles 90 is the operation target only with the voice "Take PET bottle!" Thus, it is necessary for the robot 80 to specify what the PET bottle 90 intended by the user is.

As will be described later, according to the fourth embodiment, in the case where the user utters the command, the robot 80 is capable of specifying an object corresponding to the command as the operation target from a plurality of objects. Furthermore, the robot 80 is capable of appropriately interpreting the meaning of the recognition result on the basis of the specified operation target and the recognition result of the voice. Here, the plurality of objects may have different types for the respective objects or may be all the same type. Moreover, the robot 80 is an example of the information processing apparatus and the device according to the present disclosure.

<5-2. Configuration>

The configuration according to the fourth embodiment is now described in detail. The components included in the robot 80 according to the fourth embodiment are similar to those of the robot 40 according to the second embodiment (illustrated in FIG. 12). In the following, only components having functions different from those of the second embodiment will be described.

{5-2-1. Sound Collector 150}

The sound collector 150 according to the fourth embodiment detects sound outside the robot 80 and converts it into an electrical signal. In addition, the sound collector 150 transfers the collected voice and the context information in collecting voice (e.g., the detection result of the state of the user such as a user's gesture and line of sight, etc.) to the voice recognizer 106.

{5-2-2. Disambiguation Unit 122}

The disambiguation unit 122 according to the fourth embodiment specifies an operation target on the basis of the detection result of the state of the user in collecting voice in the case where the semantic representation converted by the natural language processor 120 includes ambiguity regarding the operation target.

In one example, in a case where the voice "Take PET bottle!" is collected and a gesture such as pointing one of a plurality of PET bottles with the finger or hand is detected in collecting voice, the disambiguation unit 122 specifies a PET bottle positioned in a direction pointed by the detected gesture among a plurality of PET bottles as the operation target. In addition, in a case where the voice "Take PET bottle!" is collected and it is detected that the user's line of sight is facing one of the plurality of PET bottles in collecting voice, the disambiguation unit 122 specifies a PET bottle positioned in the direction of the detected line of sight among the plurality of PET bottles as the operation target.

{5-2-3. Controller 110}

The controller 110 according to the fourth embodiment generates a control command for performing control, in one example, to move the robot 80, to move the arm, or the like, on the basis of the result of the semantic interpretation by the semantic interpretation unit 108.

<5-3. Effect>

According to the fourth embodiment as described above, in the case where a command including ambiguity regarding the operation target is uttered, the robot 80 specifies an operation target corresponding to the command on the basis of the result of the voice recognition and the detection result of the user's state in collecting voice. Thus, in one example, even in a case where a plurality of objects are present within a range that can be detected by the robot 80, it is possible to specify the operation target intended by the user. Then, the robot 80 is capable of executing the operation related to the operation target in such a way to follow the intuition of the user on the basis of the voice recognition result.

«6. Modification»

The preferred embodiment (s) of the present disclosure is not limited to the above examples. A person skilled in the art may find various alterations and modifications within scope of the appended claims, and it should be understood that those will naturally come under the technical scope of the present disclosure.

<6-1. Modification 1>

In one example, in the first embodiment, the example in which the device according to the present disclosure is the car 10, that is, a device that moves on the ground is described, but the present disclosure is not limited to this example. In one example, the device may be a flight vehicle such as a drone. Then, in this case, the flight vehicle is capable of interpreting the meaning of the voice of the command regarding the vertical direction such as "Go up!" in addition to the command to move it back, forth, left, and right.

In one example, in a case where the voice "Go up!" is collected when the flight vehicle is set to the mode that moves while following the user, the flight vehicle may interpret the semantic representation corresponding to the recognition result of the voice as a command to move it upward with reference to the current position of the user. In addition, in a case where the voice "Go up!" is collected while the image captured by the flight vehicle is being displayed on the HMD 20 or the tablet terminal 22, the flight vehicle is capable of interpreting the semantic representation corresponding to the recognition result of the voice as a command to move it upward with reference to the current position of the flight vehicle. In other words, in this case, the flight vehicle is moved regardless of the position of the user.

<6-2. Modification 2>

Further, in the respective embodiments described above, the example in which the information processing apparatus according to the present disclosure is the car 10, the robot 40, the information processing apparatus 50, or the robot 80 is described, but it is not limited thereto. In one example, the information processing apparatus may be an agent device, a machine tool, or the like for controlling various appliances in the house.

Further, according to the respective embodiments described above, it is also possible to provide a computer program for causing hardware such as CPU, ROM, and RAM to implement a function equivalent to that of each configuration of the car 10, the robot 40, the information processing apparatus 50, or the robot 80 according to the respective embodiments described above. In addition, a recording medium on which the computer program is recorded is also provided.

Further, the effects described in this specification are merely illustrative or exemplified effects, and are not limitative. That is, with or in the place of the above effects, the technology according to the present disclosure may achieve other effects that are clear to those skilled in the art from the description of this specification.

Additionally, the present technology may also be configured as below.

(1)

An information processing apparatus including:

a semantic interpretation unit configured to interpret a meaning of a recognition result of a collected voice of a user on a basis of the recognition result and context information in collecting the voice.

(2)

The information processing apparatus according to (1), in which the voice of the user is a voice of a command directed to a device.

(3)

The information processing apparatus according to (2), in which the context information includes information indicating a positional relationship between the device and the user.

(4)

The information processing apparatus according to (3), in which the command is a command regarding a direction, and the semantic interpretation unit specifies a control direction with respect to the device on a basis of the recognition result and the positional relationship between the device and the user in collecting the voice.

(5)

The information processing apparatus according to (4), in which the context information further includes a detection result regarding a line of sight of the user, and the semantic interpretation unit specifies the control direction with respect to the device further on a basis of a detected line-of-sight direction of the user.

(6)

The information processing apparatus according to (4) or (5), in which the semantic interpretation unit specifies the control direction with respect to the device on a basis of an arrival direction of the voice detected by the device in a case where the user is determined to be located outside the device.

(7)

The information processing apparatus according to any one of (4) to (6), in which the semantic interpretation unit specifies the control direction with respect to the device on a basis of a direction in front of the device in a case where the user is determined to be located inside the device.

(8)

The information processing apparatus according to any one of (4) to (7), in which the context information further include information regarding an image displayed on a display unit.

(9)

The information processing apparatus according to (8), in which the image is an image outside the device, and the semantic interpretation unit specifies the control direction with respect to the device on a basis of a capturing direction of the image.

(10)

The information processing apparatus according to (8) or (9), in which the semantic interpretation unit specifies the control direction with respect to the device on a basis of the image displayed on the display unit in a case where the user is determined to be located remotely from the device.

(11)

The information processing apparatus according to (2), in which the context information is information indicating a relationship between a display direction and a cardinal point on a map screen displayed on a display unit.

(12)

The information processing apparatus according to (11), in which the command is a command regarding a direction, and the semantic interpretation unit specifies the control direction with respect to the device on a basis of the recognition result and the relationship between the display direction and the cardinal point on the map screen in collecting the voice.

(13)

The information processing apparatus according to (2), in which the context information is attitude information of the device.

(14)

The information processing apparatus according to (2), in which the context information is information indicating a relationship between positions of a plurality of objects corresponding to the recognition result and a direction pointed by the user.

(15)

The information processing apparatus according to (14), in which the semantic interpretation unit specifies one of the plurality of objects as an operation target on a basis of the recognition result and the relationship between the positions of the plurality of objects and the direction pointed by the user in collecting the voice.

(16)

The information processing apparatus according to (15), in which the semantic interpretation unit specifies an object located in the direction pointed by the user in collecting the voice among the plurality of objects as the operation target.

(17)

The information processing apparatus according to any one of (2) to (16), in which the context information includes information regarding a sound collector configured to collect the voice.

(18)

The information processing apparatus according to (17), in which the information regarding the sound collector is information indicating a type of the sound collector or a positional relationship between the sound collector and the device.

(19)

An information processing method including:

interpreting, by a processor, a meaning of a recognition result of a collected voice of a user on a basis of the recognition result and context information in collecting the voice.

(20)

A program causing a computer to function as:

a semantic interpretation unit configured to interpret a meaning of a recognition result of a collected voice of a user on a basis of the recognition result and context information in collecting the voice.

REFERENCE SIGNS LIST 10 car
20 HMD
22 tablet terminal
24 communication network
40, 80 robot
50 information processing apparatus
60 endoscope
100 internal sound collector
102 external sound collector
104 communication unit
106 voice recognizer
108 semantic interpretation unit
110 controller
112, 602 driving unit
120 natural language processor
122 disambiguation unit
124 natural language knowledge DB
126 disambiguation knowledge DB
150 sound collector
200 first remote sound collector
220 second remote sound collector
600 attitude sensor
604 imaging unit
606 illumination unit
650 display unit

The invention claimed is:

1. An information processing apparatus, comprising:
 a sound collector configured to:
  collect a voice of a user; and
  generate context information corresponding to the collected voice of the user, wherein the context information indicates an arrival direction of the collected voice with respect to the information processing apparatus;
 a voice recognizer configured to recognize the collected voice of the user to obtain a voice recognition result; and
 a semantic interpretation unit configured to interpret a meaning of the voice recognition result based on the context information.

2. The information processing apparatus according to claim 1, wherein the voice of the user corresponds to a voice command directed to a device.

3. The information processing apparatus according to claim 2, wherein the context information includes first information indicating a positional relationship between the device and the user.

4. The information processing apparatus according to claim 3, wherein
 the voice command corresponds to a first direction, and
 the semantic interpretation unit is further configured to specify a control direction with respect to the device based on the voice recognition result and the first information.

5. The information processing apparatus according to claim 4, wherein
 the context information further indicates line-of-sight direction of the user, and
 the semantic interpretation unit is further configured to specify the control direction with respect to the device based on the line-of-sight direction of the user.

6. The information processing apparatus according to claim 4, wherein the semantic interpretation unit is further configured to specify the control direction with respect to the device, based on the arrival direction of the collected voice and a location of the user outside the device.

7. The information processing apparatus according to claim 4, wherein the semantic interpretation unit is further configured to specify the control direction with respect to the device, based on a second direction in front of the device and a location of the user inside the device.

8. The information processing apparatus according to claim 4, wherein the context information further includes second information corresponding to an image displayed on a display unit.

9. The information processing apparatus according to claim 8, wherein
 the display unit is outside the device, and
 the semantic interpretation unit is further configured to specify the control direction with respect to the device based on a capturing direction of the image.

10. The information processing apparatus according to claim 8, wherein the semantic interpretation unit is further configured to specify the control direction with respect to the device, based on the image displayed on the display unit and a remote location of the user from the device.

11. The information processing apparatus according to claim 2, wherein the context information indicates a relationship between a display direction of a map screen displayed on a display unit and a cardinal point on the map screen.

12. The information processing apparatus according to claim 11, wherein
   the voice command corresponds to a direction, and
   the semantic interpretation unit is further configured to specify a control direction with respect to the device based on the voice recognition result and the relationship between the display direction of the map screen and the cardinal point on the map screen.

13. The information processing apparatus according to claim 2, wherein the context information includes attitude information of the device.

14. The information processing apparatus according to claim 2, wherein the context information includes information indicating a relationship between positions of a plurality of objects corresponding to the voice recognition result and a pointing direction of the user.

15. The information processing apparatus according to claim 14, wherein the semantic interpretation unit is further configured to specify one of the plurality of objects as an operation target based on the voice recognition result and the information.

16. The information processing apparatus according to claim 15, wherein the semantic interpretation unit is further configured to specify an object, of the plurality of objects, located in the pointing direction as the operation target.

17. The information processing apparatus according to claim 2, wherein the context information further includes information corresponding to the sound collector.

18. The information processing apparatus according to claim 17, wherein the information corresponding to the sound collector indicates one of a type of the sound collector or a positional relationship between the sound collector and the device.

19. An information processing method, comprising:
   in an information processing apparatus that includes a processor:
   collecting, by the processor, a voice of a user;
   generating, by the processor, context information corresponding to the collected voice of the user, wherein the context information indicates an arrival direction of the collected voice with respect to the information processing apparatus;
   recognizing, by the processor, the collected voice of the user to obtain a voice recognition result; and
   interpreting, by the processor, a meaning of the voice recognition result based on the context information.

20. A non-transitory computer-readable medium having stored thereon computer-executable instructions, which when executed by a processor of an information processing apparatus, cause the processor to execute operations, the operations comprising:
   collecting a voice of a user;
   generating context information corresponding to the collected voice of the user, wherein the context information indicates an arrival direction of the collected voice with respect to the information processing apparatus;
   recognizing the collected voice of the user to obtain a voice recognition result; and
   interpreting a meaning of the voice recognition result based on the context information.

* * * * *